US012799107B2

(12) United States Patent
Maki et al.

(10) Patent No.: US 12,799,107 B2
(45) Date of Patent: Nov. 17, 2026

(54) HETEROCYCLIC COMPOUND, SALT THEREOF, AND LUMINESCENT SUBSTRATE COMPOSITION

(71) Applicant: The University of Electro-Communications, Chofu (JP)

(72) Inventors: Shojiro Maki, Chofu (JP); Nobuo Kitada, Chofu (JP); Ryohei Moriya, Chofu (JP)

(73) Assignee: The University of Electro-Communications, Chofu-shi (JP)

( * ) Notice: Subject to any disclaimer, the term of this patent is extended or adjusted under 35 U.S.C. 154(b) by 209 days.

(21) Appl. No.: 18/870,687

(22) PCT Filed: May 25, 2023

(86) PCT No.: PCT/JP2023/019538
§ 371 (c)(1),
(2) Date: Dec. 2, 2024

(87) PCT Pub. No.: WO2023/238683
PCT Pub. Date: Dec. 14, 2023

(65) Prior Publication Data

US 2025/0368636 A1 Dec. 4, 2025

(30) Foreign Application Priority Data

Jun. 6, 2022 (JP) ................................ 2022-091845

(51) Int. Cl.
*C07D 417/10* (2006.01)
*C07D 277/587* (2006.01)
*C07D 417/14* (2006.01)

(52) U.S. Cl.
CPC ......... *C07D 417/10* (2013.01); *C07D 417/14* (2013.01)

(58) Field of Classification Search
CPC . C07D 417/10; C07D 417/14; C07D 277/587
See application file for complete search history.

(56) References Cited

FOREIGN PATENT DOCUMENTS

| | | | | |
|---|---|---|---|---|
| JP | 2009184932 A | 8/2009 | | |
| JP | 2013184909 A | 9/2013 | | |
| JP | 2014218456 A | 11/2014 | | |
| JP | 2015193584 A | 11/2015 | | |
| JP | 2016044166 A | 4/2016 | | |
| WO | 9311433 A1 | 6/1993 | | |
| WO | 2009096197 A1 | 8/2009 | | |
| WO | WO-2018118781 A1 * | 6/2018 | ........... | C07D 413/10 |
| WO | 2021193069 A1 | 9/2021 | | |

OTHER PUBLICATIONS

Dec. 12, 2024, International Preliminary Report on Patentability issued in the International Patent Application No. PCT/JP2023/019538.

Aug. 15, 2023, International Search Report issued in the International Patent Application No. PCT/JP2023/019538.

Brian G. Alberding et al., Sexithiophenes Mediated by MM Quadruple Bonds: MM = Mo2, MoW, and W2, Inorganic Chemistry, 2009, pp. 8536-8543, vol. 48.

Chihiro Miura et al., Synthesis and luminescence properties of biphenyl-type firefly luciferin analogs with a new, near-infrared light-emitting bioluminophore, Tetrahedron, 2013, pp. 9726-9734, vol. 69.

Masahiro Kiyama et al., Quantum yield improvement of red-light-emitting firefly luciferin analogues for in vivo bioluminescence imaging, Tetrahedron, 2018, pp. 652-660, vol. 74.

Veli-Matti Mukkala et al., Novel Thiazole-Containing Complexing Agents and Luminescence of Their Europium (III) and Terbium(III) Chelates, Helvetica Chimica Acta, 1996, pp. 295-306, vol. 79.

Zi Yao et al., Multicomponent Bioluminescence Imaging with a π-Extended Luciferin, Journal of the American Chemical Society, 2020, pp. 14080-14089, vol. 142.

* cited by examiner

*Primary Examiner* — Matthew P Coughlin
(74) *Attorney, Agent, or Firm* — KENJA IP LAW PC

(57) ABSTRACT

Provided is a heterocyclic compound represented by the following general formula (1):

(1)

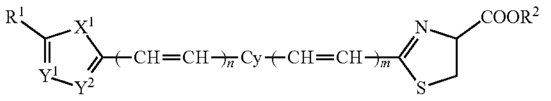

where Cy has a specific ring structure, $R^1$ is $—NR^5R^6$, $—OR^7$, or hydrogen, and $R^5$, $R^6$, and $R^7$ are each independently hydrogen or an alkyl group having 1 to 4 carbon atoms; $R^5$ and $R^6$ may bond together to form a ring, or one of $R^5$ and $R^6$ may form a ring by bonding with $Y^1$, $R^2$ is hydrogen or an alkyl group having 1 to 4 carbon atoms, $X^1$ is S, O, $NR^8$, or $CH_2$, $Y^1$ and $Y^2$ are each independently N or $CR^8$, where $R^8$ is each independently hydrogen, an alkyl group having 1 to 4 carbon atoms, an alkenyl group having 2 to 4 carbon atoms, or an acyl group having 2 to 4 carbon atoms, and n and m are each independently an integer of 0 to 3.

9 Claims, 3 Drawing Sheets

HETEROCYCLIC COMPOUND, SALT THEREOF, AND LUMINESCENT SUBSTRATE COMPOSITION

TECHNICAL FIELD

The present disclosure relates to a novel heterocyclic compound, a salt thereof, and a luminescent substrate composition.

BACKGROUND

Visualization of the inside of a living organism is a significant challenge in the field of life sciences, and research using bioluminescent systems visualization of the inside of a living organism has been conducted. Among such bioluminescent systems, the luminescent system of fireflies is known as a luminescent system with excellent luminescence efficiency. In this firefly luminescent system, the luminescent substrate, firefly luciferin ($LH_2$), is converted into an excited state oxyluciferin in the presence of the luminescent enzyme, firefly luciferase (Luc), adenosine triphosphate (ATP), and magnesium ions ($Mg^{2+}$), and yellow-green light with a wavelength of approximately 560 nm is emitted when the oxyluciferin deactivates to its ground state.

Recently, compounds that achieve a variety of luminescent wavelengths have been synthesized as analogs of the luminescent substrates of the firefly luminescent system. For example, the luminescent substrates with molecular structures similar to firefly luciferin are disclosed in PTLs 1 to 4 below. Among these firefly luciferin analogs, luminescent substrates that emit long-wavelength light are promising as labeling materials for visualizing lesions deep inside living organisms, because long-wavelength light has high transmittance within living organisms. For example, PTLs 1 to 3 disclose compounds showing an emission spectrum with a peak wavelength of approximately 670 nm, while PTL 4 discloses a compound showing an emission spectrum with a peak wavelength of approximately 760 nm. These materials enable the visualization of small cells deep inside living organisms, which could not previously be imaged using light-based techniques.

CITATION LIST

Patent Literature

PTL 1: JP 2009-184932 A
PTL 2: JP 2014-218456 A
PTL 3: JP 2015-193584 A
PTL 4: WO 2021/193069 A1

SUMMARY

Technical Problem

As mentioned above, various compounds with novel structures have been proposed as luminescent substrates in firefly bioluminescent systems, but only a limited number of compounds have been commercialized as materials capable of near-infrared luminescent labeling.

Therefore, the present disclosure is directed to providing a novel compound that can be used as a luminescent substrate in a firefly bioluminescent system.

Additionally, the present disclosure is also directed to providing a novel compound that is capable of emitting long-wavelength light and can be used as a luminescent substrate in a firefly bioluminescent system.

Solution to Problem

The present inventors have conducted extensive research to solve the above problem and found that compounds with a specific structure or salts thereof function as luminescent substrates in firefly bioluminescent systems, thereby completing the present disclosure.

Namely, the gist of the present disclosure for solving the above problem is as follows.

[1] A heterocyclic compound represented by the following general formula (1):

[Chem. 1]

(1)

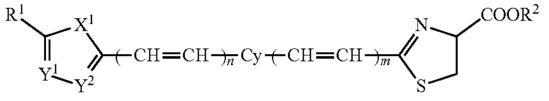

where Cy is represented by the following general formula (2-1) or (2-2):

[Chem. 2]

(2-1)

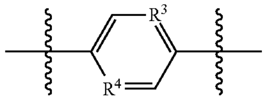

(2-2)

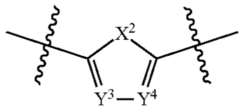

$R^1$ is $-NR^5R^6$, $-OR^7$, or hydrogen, and $R^5$, $R^6$, and $R^7$ are each independently hydrogen or an alkyl group having 1 to 4 carbon atoms; $R^5$ and $R^6$ may bond together to form a ring, or one of $R^5$ and $R^6$ may bond with $Y^1$ to form a ring, $R^2$ is hydrogen or an alkyl group having 1 to 4 carbon atoms, $R^3$ and $R^4$ are each independently CH or N, $X^1$ and $X^2$ are each independently S, O, $NR^8$, or $CH_2$, $Y^1$, $Y^2$, $Y^3$, and $Y^4$ are each independently N or $CR^8$, where $R^8$ is each independently hydrogen, an alkyl group having 1 to 4 carbon atoms, an alkenyl group having 2 to 4 carbon atoms, or an acyl group having 2 to 4 carbon atoms, and n and m are each independently an integer of 0 to 3.

The heterocyclic compound of the present disclosure according to the above [1] functions as a luminescent substrate in a firefly bioluminescent system.

[2] The heterocyclic compound according to [1], wherein $X^1$ is S, O, or $NR^8$.

According to the heterocyclic compound according to the above [2], the luminescence efficiency is improved.

[3] The heterocyclic compound according to [1] or [2], wherein $Y^1$ and $Y^2$ are each independently $CR^8$.

According to the heterocyclic compound according to the above [3], the luminescence efficiency is improved.

[4] The heterocyclic compound according to any one of [1] to [3], wherein Cy is represented by the above general formula (2-1).

The heterocyclic compound according to the above [4] can be synthesized easily.

[5] A heterocyclic compound according to any one of [1] to [4], which is represented by any of the following structural formulas (1-1) to (1-10):

[Chem. 3-1]

(1-1)

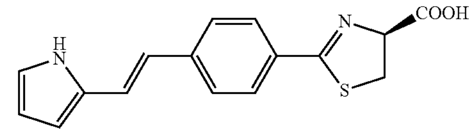

(1-2)

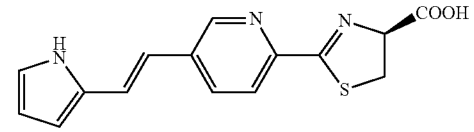

(1-3)

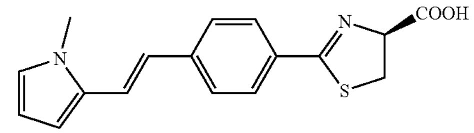

(1-4)

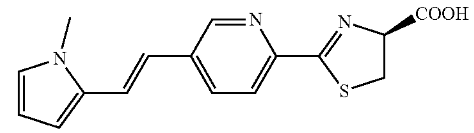

(1-5)

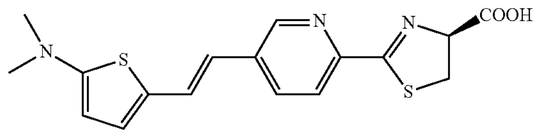

[Chem. 3-2]

(1-6)

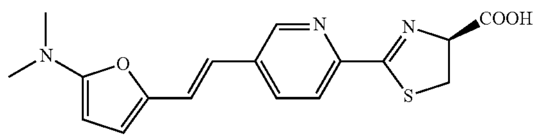

(1-7)

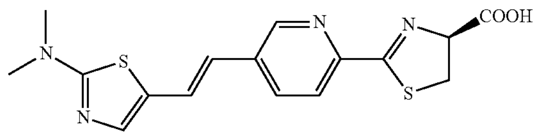

(1-8)

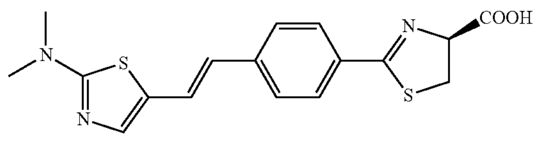

-continued (1-9)

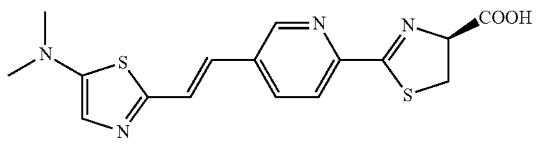

(1-10)

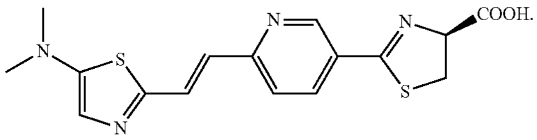

Since the heterocyclic compound according to the above [5] is capable of emitting long-wavelength light, it is particularly useful for the visualization of deep areas inside living organisms.

[6] A salt of the heterocyclic compound according to any one of [1] to [5].

Since the salt of the heterocyclic compound according to the above [6] has excellent solubility in water and neutral pH buffer solutions, it can be dissolved at high concentrations.

[7] A luminescent substrate composition comprising the heterocyclic compound according to any one of [1] to [5] or the salt according to [6].

The luminescent substrate composition of the present disclosure according to the above [7] can form a firefly bioluminescence system together with a luminescent enzyme.

Advantageous Effect

According to the present disclosure, it is possible to provide a heterocyclic compound and a salt thereof that can be used as a luminescent substrate in a firefly bioluminescent system.

Furthermore, according to one embodiment of the present disclosure, it is possible to provide a heterocyclic compound and a salt thereof that is capable of emitting long-wavelength light and used as a luminescent substrate in a firefly bioluminescent system.

DETAILED DESCRIPTION

Figure 1:
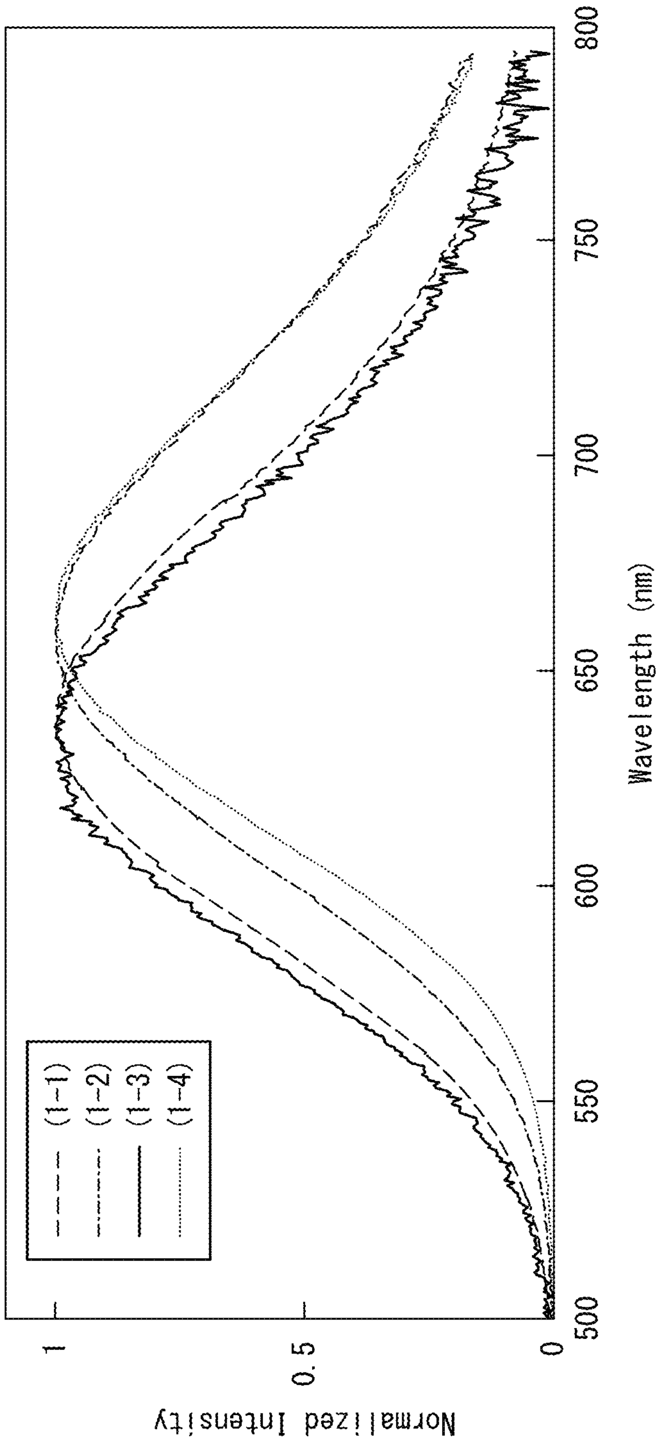
FIG. 1 illustrates emission spectra normalized so that the maximum emission intensity was 1 in a luminescent system using the compound represented by the structural formula (1-1), the compound represented by the structural formula (1-2), the compound represented by the structural formula (1-3), or the compound represented by the structural formula (1-4) as the luminescent substrate.

The following provides a detailed description of a heterocyclic compound and a salt thereof, and a luminescent substrate composition of the present disclosure, with reference to an embodiment thereof.

Heterocyclic Compound and Salt Thereof

The heterocyclic compound of the present disclosure is represented by the following general formula (1):

[Chem. 4]

(1)

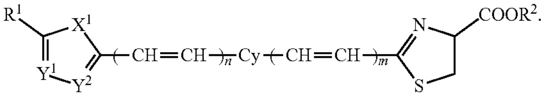

Since the heterocyclic compound of the present disclosure contains a dihydrothiazole ring, and also contains another five-membered ring and an additional ring structure (Cy) which can be either a five- or six-membered ring, and its molecular structure is similar to firefly luciferin, it functions as a luminescent substrate in a firefly bioluminescent system. Additionally, heterocyclic compounds in which at least one of n and m in the above general formula (1) is not zero function as luminescent substrates in firefly bioluminescent systems and are capable of emitting long-wavelength light.

The heterocyclic compounds represented by the above general formula (1) can also be in the form of salts, which also function as luminescent substrates in a firefly bioluminescent system.

In the above general formula (1), $R^1$ is —$NR^5R^6$, —$OR^7$, or hydrogen, and $R^5$, $R^6$, and $R^7$ are each independently hydrogen or an alkyl group having 1 to 4 carbon atoms; $R^5$ and $R^6$ may bond together to form a ring, or one of $R^5$ and $R^6$ may form a ring by bonding with $Y^1$.

Here, examples of alkyl groups having 1 to 4 carbon atoms include methyl, ethyl, n-propyl, isopropyl, n-butyl, isobutyl, sec-butyl, and tert-butyl groups. From the viewpoint of luminescence efficiency, methyl groups are preferred as $R^5$ and $R^6$.

Additionally, the ring formed by $R^5$ and $R^6$ bonding together with N is preferably a three- to seven-membered ring. Examples of the group formed by $R^5$ and $R^6$ bonding together with N include 1-azacyclopropyl group (three-membered ring), 1-azacyclobutyl group (four-membered ring), 1-azacyclopentyl group (five-membered ring), 1-azacyclohexyl group (six-membered ring), and 1-azacycloheptyl group (seven-membered ring) represented by the following formulas.

[Chem. 5]

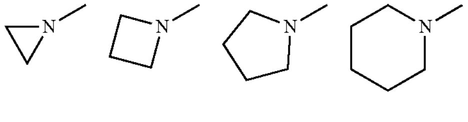

-continued

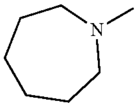

Furthermore, the ring formed by one of $R^5$ and $R^6$ bonding with $Y^1$ is preferably a five- or six-membered ring; in this case, $Y^1$ is $CR^8$, and one of $R^5$ and $R^6$ bonds with $R^8$ to form a ring structure.

In the above general formula (1), $R^2$ is hydrogen or an alkyl group having 1 to 4 carbon atoms. Here, examples of alkyl groups having 1 to 4 carbon atoms include methyl, ethyl, n-propyl, isopropyl, n-butyl, isobutyl, sec-butyl, and tert-butyl groups. From the viewpoint of luminescence efficiency, hydrogen is preferred as $R^2$.

In the above general formula (1), $X^1$ is S, O, $NR^8$, or $CH_2$, and $Y^1$ and $Y^2$ are each independently N or $CR^8$.

From the viewpoint of luminescence efficiency, $X^1$ is preferably S, O, or $NR^8$.

Similarly, from the viewpoint of luminescence efficiency, $Y^1$ and $Y^2$ are each preferably $CR^8$.

With regard to $X^1$, $Y^1$, and $Y^2$ in the above general formula (1), $R^8$ is each independently hydrogen, an alkyl group having 1 to 4 carbon atoms, an alkenyl group having 2 to 4 carbon atoms, or an acyl group having 2 to 4 carbon atoms. When one or both of $Y^1$ and $Y^2$ are $CR^8$, $R^8$ is preferably hydrogen.

Here, examples of alkyl groups having 1 to 4 carbon atoms include methyl, ethyl, n-propyl, isopropyl, n-butyl, isobutyl, sec-butyl, and tert-butyl groups.

Examples of alkenyl groups having 2 to 4 carbon atoms include vinyl ($CH_2$═CH—), allyl ($CH_2$═$CHCH_2$—), 1-propenyl ($CH_3CH$═CH—), isopropenyl ($CH_2$═C($CH_3$)—), 1-butenyl ($CH_3CH_2CH$═CH—), 2-butenyl ($CH_3CH$═$CHCH_2$—), and 3-butenyl ($CH_2$═$CHCH_2CH_2$—) groups.

Examples of acyl groups having 2 to 4 carbon atoms include acetyl ($CH_3$—CO—), propionyl ($CH_3CH_2$—CO—), butyryl ($CH_3CH_2CH_2$—CO—), isobutyryl (($CH_3)_2CH$—CO—), acryloyl ($CH_2$═CH—CO—), and methacryloyl ($CH_2$═C($CH_3$)—CO—) groups.

In the above general formula (1), n and m are each independently an integer of 0 to 3. Here, n and m indicate the number of repeating vinylene units (—CH═CH—), and the greater the number of n and/or m, the longer the emission wavelength. From the viewpoint of achieving longer emission wavelengths and visualization of deep areas inside living organisms, it is preferred that at least one of n and m is not 0.

The optimal wavelength for bioimaging (i.e., a wavelength suitable for biological transparency) is 600 to 900 nm because it is less affected by the scattering and absorption of hemoglobin, oxidized hemoglobin, and water. Therefore, from the viewpoint of visualization of deep areas inside living organisms, n is preferably 1, 2, or 3, while from the viewpoint of ease of synthesis, n is preferably 0, 1, or 2. Similarly, from the viewpoint of visualization of deep areas inside living organisms, m is preferably 1, 2, or 3, while from the viewpoint of ease of synthesis, m is preferably 0, 1, or 2.

Each vinylene unit may be connected via trans-type bonds, may be connected via cis-type bonds, or may be connected via a mixture of trans-type bonds and cis-type bonds. From the viewpoint of luminescence efficiency, it is preferred that each vinylene unit is connected via trans-type bonds.

In the above general formula (1), Cy is represented by the following general formula (2-1) or (2-2):

[Chem. 6]

(2-1)

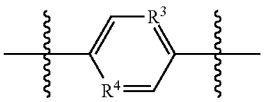

(2-2)

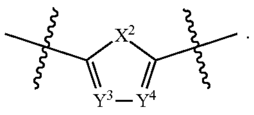

From the viewpoint of ease of synthesis, Cy is preferably represented by the above general formula (2-1).

In the above general formula (2-1), $R^3$ and $R^4$ are each independently CH or N. Here, when at least one of $R^3$ and $R^4$ is N, the water solubility of the heterocyclic compound is improved and luminescence intensity is also improved.

In the above general formula (2-2), $X^2$ is S, O, $NR^8$, or $CH_2$, and $Y^3$ and $Y^4$ are each independently N or $CR^8$.

With regard to $X^2$, $Y^3$, and $Y^4$ in the above general formula (2-2), $R^8$ is each independently hydrogen, an alkyl group having 1 to 4 carbon atoms, an alkenyl group having 2 to 4 carbon atoms, or an acyl group having 2 to 4 carbon atoms. When one or both of $Y^3$ and $Y^4$ are $CR^8$, $R^8$ is preferably hydrogen.

Here, examples of alkyl groups having 1 to 4 carbon atoms include methyl, ethyl, n-propyl, isopropyl, n-butyl, isobutyl, sec-butyl, and tert-butyl groups.

Examples of alkenyl groups having 2 to 4 carbon atoms include vinyl ($CH_2{=}CH{-}$), allyl ($CH_2{=}CHCH_2{-}$), 1-propenyl ($CH_3CH{=}CH{-}$), isopropenyl ($CH_2{=}C(CH_3){-}$), 1-butenyl ($CH_3CH_2CH{=}CH{-}$), 2-butenyl ($CH_3CH{=}CHCH_2{-}$), and 3-butenyl ($CH_2{=}CHCH_2CH_2{-}$) groups.

Examples of acyl groups having 2 to 4 carbon atoms include acetyl ($CH_3{-}CO{-}$), propionyl ($CH_3CH_2{-}CO{-}$), butyryl ($CH_3CH_2CH_2{-}CO{-}$), isobutyryl ($(CH_3)_2CH{-}CO{-}$), acryloyl ($CH_2{=}CH{-}CO{-}$), and methacryloyl ($CH_2{=}C(CH_3){-}CO{-}$) groups.

As the heterocyclic compound represented by the above general formula (1), compounds represented by the following structural formulas (1-1) to (1-10) are particularly preferred.

[Chem. 7-1]

(1-1)

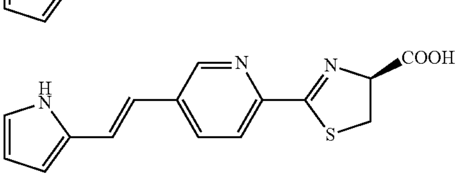

(1-2)

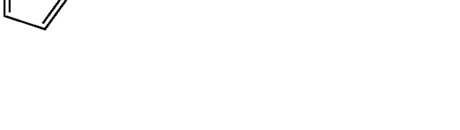

-continued (1-3)

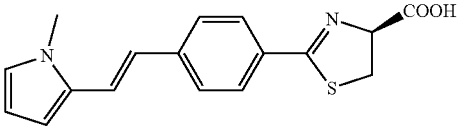

(1-4)

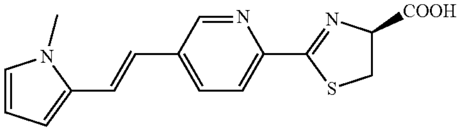

(1-5)

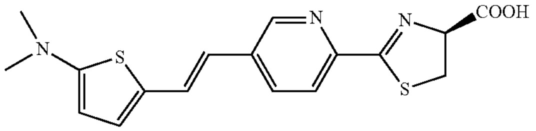

[Chem. 7-2]

(1-6)

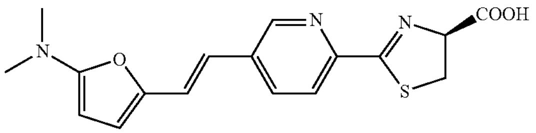

(1-7)

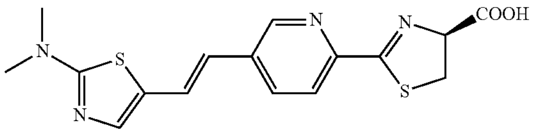

(1-8)

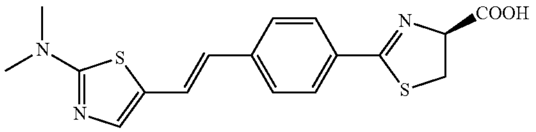

(1-9)

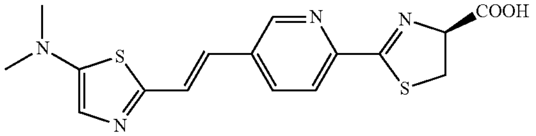

(1-10)

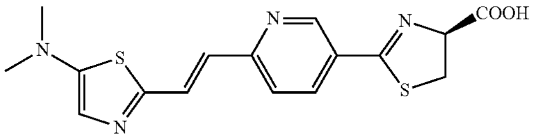

The heterocyclic compounds and salts thereof represented by the above structural formulas (1-1) to (1-10) are particularly useful for the visualization of deep areas inside living organisms because they function as luminescent substrates in firefly bioluminescent systems and are also capable of emitting long-wavelength light. Additionally, the heterocyclic compounds and salts thereof represented by the above structural formulas (1-5) or (1-6) are particularly useful for the visualization of deep areas inside living organisms because they can emit especially long-wavelength light. Furthermore, by combining a heterocyclic compound and salt thereof that emit long-wavelength light with a luminescent substrate that emits blue light, firefly luciferin ($LH_2$)

that emits yellow-green light, or other substances, multicolor multiplex imaging that simultaneously visualizes multiple phenomena within a living organism becomes possible.

The heterocyclic compounds represented by the above general formula (1) are not particularly limited but can be synthesized as follows.

For example, a five-membered ring compound having an aldehyde group, such as pyrrole-2-carboxaldehyde, is used as a starting material, which is Boc-protected using di-tert-butyl dicarbonate, if desired. Next, after performing a Wittig reaction using a Wittig reagent (e.g., $CNPhCH_2PPh_3$), the Boc protection is removed by adding an aqueous sodium hydroxide solution, if desired, to obtain a cyano compound (nitrile compound).

Alternatively, a five-membered ring compound having an aldehyde group, such as 1-methyl-2-pyrrolecarboxaldehyde or 2-thiophenecarboxaldehyde, is used as a starting material, and a Wittig reaction is performed on the starting compound to obtain a cyano compound (nitrile compound).

Alternatively, a five-membered ring compound having an aldehyde group, such as 1-methyl-2-pyrrolecarboxaldehyde or furfural, is used as a starting material, and a Horner-Wadsworth-Emmons (HWE) reaction is performed using an HWE reagent on the starting compound to obtain a cyano compound (nitrile compound).

Alternatively, a five-membered ring compound having an aldehyde group, such as 5-bromo-2-thiophenecarboxaldehyde or 5-bromo-2-furfuraldehyde, is used as a starting material, which is reacted with dimethylamine, etc., to obtain a dimethylamino compound. The dimethylamino compound is then subjected to an HWE reaction using an HWE reagent to obtain a cyano compound (nitrile compound). The five-membered ring compounds having an aldehyde group can also be synthesized and used by various methods. For example, a five-membered ring compound having an aldehyde group can be synthesized by reacting the five-membered compound with a lithium compound such as lithium diisopropylamide (LDA) or lithium bis(trimethylsilyl)amide (LiHMDS), followed by reaction with a formylating agent such as N,N-dimethylformamide (DMF).

The cyano compound (nitrile compound) obtained as described above is subjected to thiazoline ring formation using D-cysteine hydrochloride hydrate to synthesize the heterocyclic compound represented by the general formula (1).

In addition, the desired heterocyclic compound can be obtained by appropriately changing the starting material, introducing various substituents, or using other synthetic routes.

The heterocyclic compound represented by the above general formula (1) can also form a salt. That is, the salt of the heterocyclic compound of the present disclosure is a salt of a heterocyclic compound represented by the above general formula (1). This salt of the heterocyclic compound of the present disclosure also functions as a luminescent substrate in a firefly bioluminescent system.

Here, the salt of the heterocyclic compound of the present disclosure may be an addition salt with an acid or an addition salt with a base. For example, in the addition salt with the heterocyclic compound of the present disclosure and the acid, examples of the acid include hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, pamoic acid, stearic acid, glutamic acid, aspartic acid, methanesulfonic acid, ethanedisulfonic acid, p-toluenesulfonic acid, salicylic acid, succinic acid, and trifluoroacetic acid. Examples of acid addition salts include hydrochloride, hydrobromide, hydroiodide, sulfate, sulfamate, phosphate, nitrate, phosphite, nitrite, citrate, formate, acetate, oxalate, maleate, lactate, tartrate, fumarate, benzoate, mandelate, cinnamate, pamoate, stearate, glutamate, aspartate, methanesulfonate, ethanedisulfonate, p-toluenesulfonate, salicylate, succinate, and trifluoroacetate. On the other hand, in the addition salt of the heterocyclic compound of the present disclosure with the base, examples of the base include sodium hydroxide, potassium hydroxide, and calcium hydroxide. Examples of base addition salts include sodium salts, potassium salts, and calcium salts.

The salt of the heterocyclic compound represented by the above general formula (1) has excellent solubility in water or a buffer solution with a pH near neutral. Therefore, the salt of the heterocyclic compound represented by the above general formula (1) can be dissolved in high concentrations in water or a buffer solution with a pH near neutral, thereby improving luminescence intensity.

Luminescent Substrate Composition

A luminescent substrate composition of the present disclosure includes a heterocyclic compound represented by the above-mentioned general formula (1) or a salt thereof and may consist solely of a heterocyclic compound represented by the above-mentioned general formula (1) or salt thereof. The luminescent substrate composition of the present disclosure can form a firefly bioluminescent system together with a luminescent enzyme such as natural firefly luciferase (Luc) or mutant enzymes thereof.

The heterocyclic compound and salt thereof of the present disclosure described above emit light upon oxidation by luminescent beetle luciferase when added to a system containing luminescent beetle luciferase, adenosine triphosphate (ATP), and magnesium ions ($Mg^{2+}$). Furthermore, the heterocyclic compound and salt thereof of the present disclosure can be provided as a luminescence detection kit (luminescent substrate composition) along with ATP and $Mg^{2+}$. The luminescence detection kit may also include other luminescent substrates and a solution adjusted to an appropriate pH.

When the heterocyclic compound and salt thereof of the present disclosure is applied to a luminescent system, the heterocyclic compound and salt thereof is preferably used at a concentration of 1 μM or higher, and is more preferably used at a concentration of 5 μM or higher, to obtain a suitable luminescent intensity. That is, the luminescent substrate composition of the present disclosure contains the heterocyclic compound represented by the above-mentioned general formula (1) or salt thereof preferably at a concentration of 1 μM or higher, more preferably at a concentration of 5 μM or higher. Additionally, the pH of the luminescent substrate composition of the present disclosure and the pH of the luminescent system are preferably 4 to 10, more preferably 6 to 8. If necessary, a buffering agent such as potassium phosphate, tris hydrochloride, glycine, or HEPES may be contained to stabilize the pH. Additionally, if the luminescent substrate composition (luminescence detection kit) contains ATP, the concentration of ATP is preferably 4 μM or higher, more preferably 20 μM or higher.

Moreover, the heterocyclic compound and salt thereof of the present disclosure can be made to emit light in the firefly luminescent beetle luciferase bioluminescent system by various luminescent enzymes (oxidases). Luciferases have been isolated from the North American firefly (*Photinus pyralis*), the railroad worm, and other sources, all of which can be used. Examples of oxidases that can be used include pyrophorus noctiluca luciferase, Rhagophthalmus ohbai luciferase, and flavin-containing monooxygenase. Additionally, mutant enzymes of natural firefly luciferase can also be used as luminescent enzymes.

The bioluminescence using the heterocyclic compound and salt thereof of the present disclosure as a luminescent substrate is enhanced when coenzyme A (CoA), pyrophosphoric acid, or magnesium ions ($Mg^{2+}$) are present in the luminescent system. The luminescence enhancement effect of these compounds is remarkable when the concentration of each of CoA, pyrophosphoric acid, or $Mg^{2+}$ in the luminescent system is 5 μM or higher, and the luminescence is enhanced as the concentration increases.

To use the firefly bioluminescent system for measurement/detection, it is preferable to stabilize the luminescence to prevent enzyme deactivation and to exhibit plateau-like luminescent behavior. For example, it is preferable to have magnesium ions present in the luminescent system, and it is even more preferable to have both magnesium ions and pyrophosphoric acid present together. In the case when magnesium ions are used alone, from the viewpoint of stabilization of luminescence, the concentration of magnesium ions in the luminescent system is preferably 0.5 mM or higher, and the stability of luminescence improves as the concentration increases.

When magnesium pyrophosphate is used, the concentration of magnesium pyrophosphate in the luminescent system is preferably 10 μM or higher, more preferably 100 μM or higher, from the viewpoint of stabilization of luminescence. The ratio between pyrophosphoric acid and magnesium ions does not need to be an equivalent ratio. Preferred magnesium salts include inorganic acid salts such as magnesium sulfate and magnesium chloride, as well as organic acid salts such as magnesium acetate, etc. Preferred pyrophosphates include pyrophosphates of alkali metals such as sodium and potassium, pyrophosphates of alkaline earth metals such as magnesium and calcium, pyrophosphates of iron, etc.

The heterocyclic compound and salt thereof of the present disclosure can be used as luminescent labels in biological measurement/detection and, for example, can be used to label amino acids, polypeptides, proteins, nucleic acids, and other substances. The method of binding the heterocyclic compound or salt thereof of the present disclosure to these substances is well known to those skilled in the art. For example, the heterocyclic compound or salt thereof of the present disclosure can be bound to a carboxyl or amino group of the target substance using methods well known to those skilled in the art.

Furthermore, the heterocyclic compound and salt thereof of the present disclosure can be used in measurement/detection that utilizes the detection of luminescent beetle luciferase activity based on the luminescence of the luminescent substrate. For example, by administering the heterocyclic compound or salt thereof of the present disclosure to cells or animals into which the luciferase gene has been introduced, it is possible to measure/detect the expression of the target gene or protein in vivo. Long-wavelength light has high light transmissibility and high tissue permeability. Therefore, among heterocyclic compounds and salts thereof of the present disclosure, heterocyclic compounds and salts thereof with long-wavelength luminescence are useful as labeling materials for visualizing deep areas inside living organisms.

Examples

The present disclosure is further explained in detail by the following examples, but the present disclosure is not limited to these examples.

Instrumental Analyses and Measurement Devices

1H Nuclear Magnetic Resonance Spectroscopy (1H-NMR)

The measurement was conducted using ECA 500 (500 MHz) manufactured by JEOL Ltd., and the results were recorded as "1H-NMR (measurement frequency, solvent) chemical shift values (number of hydrogens, multiplicity, spin coupling constant)." The chemical shift values (δ) were indicated in ppm, using tetramethylsilane (δ=0) as the internal standard. The multiplicity was indicated as s (singlet), d (doublet), t (triplet), q (quartet), m (multiplet or complex overlapping signals), and broad signals were marked with "br." Spin coupling constants (J) were expressed in Hz.

Mass Spectrometry (MS): Electrospray Ionization Technique (ESI)

The measurement was conducted using a TOF mass spectrometer model JMS-T100LC (AccuTOF) manufactured by JEOL Ltd. with an electrospray ionization technique (ESI). The device settings were: desolvation gas at 250 °C, needle voltage at 2000 V, ring lens voltage at 10 V, orifice 1 voltage at 80 V, and orifice 2 voltage at 5 V. Sample injection was performed via infusion at a flow rate of 20 μl/min. The results were recorded as "ESI-MS: m/z [M+adduction] mass number."

Mass Spectrometry (MS): Matrix-Assisted Laser Desorption/Ionization Technique (MALDI)

The measurement was conducted using a matrix-assisted laser desorption/ionization time-of-flight mass spectrometer JMS-S3000 Spiral TOFTM-plus 2.0 manufactured by JEOL Ltd. α-Cyano-4-hydroxycinnamic acid was used as the matrix. The results were recorded as "HR-MALDI-MS: m/z [M+adduction]+Calculated for the molecular formula; Found."

Method for Producing Compound Represented by Structural Formula (1-1)

Synthesis of Boc-Protected Compound (4)

Pyrrole-2-carboxaldehyde (3) (4.5 g, 47.3 mmol), di-tert-butyl dicarbonate (12.4 g, 56.8 mmol), triethylamine (23.0 mL, 165.6 mmol) were dissolved in methylene chloride (50 mL), and the mixture was stirred for 4 hours at room temperature under an argon atmosphere. Thereafter, 1-methylpiperazine (1 mL, 9.5 mmol) was added, and the mixture was stirred for an additional hour at room temperature. The reaction was then quenched by adding distilled water. The resultant was extracted with chloroform (30 mL×3), and the organic layer was then dried over sodium sulfate and concentrated under reduced pressure. The residue was purified by silica gel column chromatography (silica gel: 36.0 g, hexane:ethyl acetate=5:1) to obtain the Boc-protected compound (4) (6.7 g, 34.5 mmol, 73%) as a yellow oily substance.

[Chem. 8]

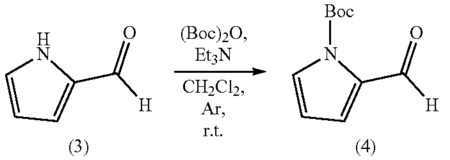

(3) (4)

Identification Result of Boc-Protected Compound (4)

1H-NMR (500 MHz, $CDCl_3$) δ=10.31 (s, 1H), 7.43 (dd, J=1.7, 2.9 Hz, 1H), 7.18 (dd, J=1.7, 3.5 Hz, 1H), 6.28 (t, J=3.5 Hz, 1H), 1.64 (s, 9H)

ESI-MS: m/z [M+Na]+; 218.06

Synthesis of Phosphorous Ylide Compound (6)

4-Cyanobenzyl bromide (5) (1.00 g, 5.10 mmol) and triphenylphosphine (1.60 g, 6.12 mmol) were dissolved in o-xylene (25 mL), and the mixture was refluxed by heating for 4 hours. The reaction mixture was cooled on ice and then washed with toluene (5 mL) to obtain the crude phosphorous ylide compound (6) (2.10 g).

[Chem. 9]

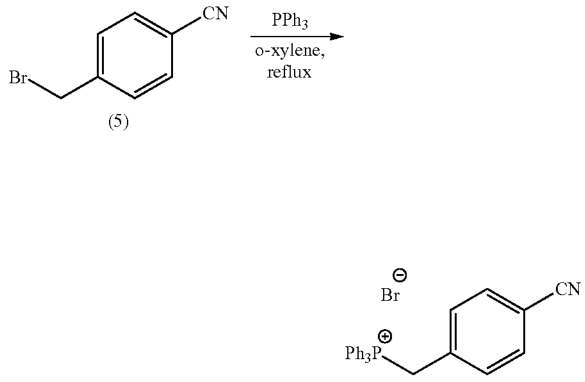

(5)

(6)

Synthesis of Cyano Compound (7a)

The phosphorous ylide compound (6) (469.7 mg, 1.02 mmol) and NaH (80.0 mg, 2.04 mmol) were dissolved in THF, and the mixture was cooled to 0 °C and stirred for 1 hour. Then, the Boc-protected compound (4) (100.0 mg, 0.51 mmol) was dissolved, and the mixture was stirred for 3 hours. Thereafter, the reaction was quenched with 2 mL of MeOH, and 2 mL of 6 M NaOH was added dropwise. The resultant was extracted with chloroform (50 mL×3), and the organic layer was then dried over sodium sulfate and concentrated under reduced pressure. The residue was purified by silica gel column chromatography (silica gel: 50.0 g, hexane:ethyl acetate=3:1) to obtain the cyano compound (7a) (14.7 mg, 0.076 mmol, 15%) as a yellow solid.

[Chem. 10]

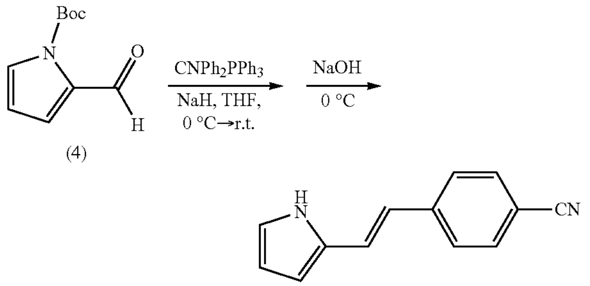

(4)

(7a)

Identification Result of Cyano Compound (7a)

1H-NMR (500 MHz, $CDCl_3$) δ=8.46 (s, 1H), 7.59 (d, J=8.5 Hz, 2H), 7.48 (d, J=8.5 Hz, 2H), 7.08 (d, J=16 Hz, 1H), 6.88 (m, 1H), 6.63 (d, J=16 Hz, 1H), 6.45 (m, 1H), 6.28 (m, 1H)

HR-MALDI-MS: m/z $[M+H]^+$ Calculated for $C_{13}H_{11}N_2$: 195.09141; Found: 195.09167.

Synthesis of Compound Represented by Structural Formula (1-1)

The cyano compound (7a) (20.3 mg, 0.11 mmol), D-cysteine hydrochloride hydrate (20.3 mg, 0.12 mmol), and potassium carbonate (21.7 mg, 0.16 mmol) were dissolved in EtOH (1 mL) and distilled water (1 mL), and the mixture was stirred at 70 °C for 17 hours. The residue was then purified by automated preparative medium-pressure column chromatography (smart flash EPCLC Al-580S ULTRA-PACK COLUMNS $C_{18}$, $H_2O$/methanol=95/5) to obtain the compound represented by the structural formula (1-1) (9.6 mg, 0.032 mmol, 31%) as a yellow solid.

[Chem. 11]

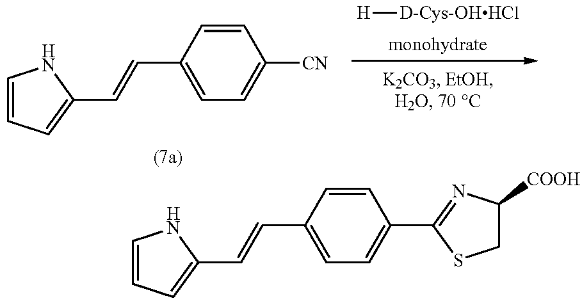

(7a)

(1-1)

Identification Result of Compound Represented by Structural Formula (1-1)

1H-NMR (500 MHz, $CD_3OD$) δ=7.81 (d, J=9 Hz, 2H), 7.48 (d, J=8.5 Hz, 2H), 7.11 (d, J=16.5 Hz, 1H), 6.80 (m, 1H), 6.78 (d, J=16 Hz, 1H), 6.30 (m, 1H), 6.123-6.118 (m, 1H), 5.08 (t, J=9 Hz, 1H), 3.67 (t, J=10 Hz, 1H), 3.60 (t, J=9 Hz, 1H)

HR-MALDI-MS: m/z $[M+H]^+$ Calculated for $C_{16}H_{15}N_2O_2S$: 299.08953; Found: 299.08487.

Method for Producing Compound Represented by Structural Formula (1-2)

Synthesis of Monobromo Compound (9)

5-Methyl-2-pyridinecarbonitrile (8) (2.0 g, 16.9 mmol), NBS (3.0 g, 16.9 mmol), and AIBN (138.7 mg, 0.85 mmol) were dissolved in carbon tetrachloride (40 mL). The mixture was placed under an argon atmosphere and refluxed by heating at 85 °C for 2 hours. The reaction was then quenched with sodium thiosulfate aqueous solution. The resultant was extracted with ethyl acetate (15 mL×3), and the organic layer was dried over sodium sulfate and concentrated under reduced pressure. The residue was purified by silica gel column chromatography (silica gel: 92 g, hexane:ethyl acetate=3:1) to obtain the monobromo compound (9) (1.3 g, crude).

[Chem. 12]

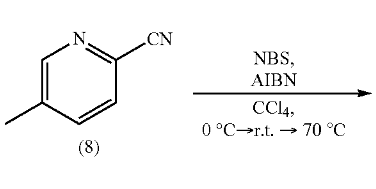

(8) (9)

Identification Result of Monobromo Compound (9)

1H-NMR (500 MHz, $CDCl_3$) δ 8.73 (d, J=2.3 Hz, 1H), 7.88 (dd, J=8.0, 2.3 Hz, 1H), 7.70 (d, J=8.0 Hz, 1H), 4.49 (s, 2H)

Synthesis of Phosphorous Ylide Compound (10)

The monobromo compound (9) (1.87 g, 9.5 mmol) and triphenylphosphine (3.73 g, 14.3 mmol) were dissolved in o-xylene (12 mL), and the mixture was refluxed by heating for 6 hours. The reaction mixture was cooled on ice and washed with hexane (10 mL) to obtain the crude phosphorous ylide compound (10).

[Chem. 13]

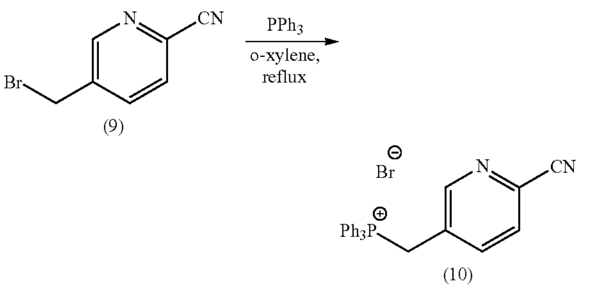

(9) (10)

Synthesis of Cyano Compound (7b)

The Boc-protected compound (4) was synthesized using the method described in the section of "Method for Producing Compound Represented by Structural Formula (1-1)."

The phosphorous ylide compound (10) (375.8 mg, 1.02 mmol) and NaH (105.3 mg, 2.14 mmol) were dissolved in THF, and the mixture was cooled to 0 °C and stirred for 1 hour. Then, the Boc-protected compound (4) (100 mg, 0.51 mmol) was dissolved, and the mixture was stirred for 1 hour. The reaction was then quenched with distilled water. The resultant was extracted with ethyl acetate (50 mL×3), and the organic layer was then dried over sodium sulfate and concentrated under reduced pressure. The residue was purified by silica gel column chromatography (silica gel: 30.8 g, hexane:ethyl acetate=3:1) to obtain the cyano compound (7b) (15.2 mg, 0.078 mmol, 15%) as a brown solid.

[Chem. 14]

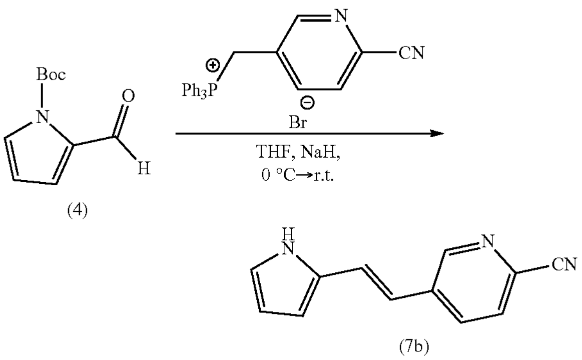

(4) (7b)

Identification Result of Cyano Compound (7b)

1H-NMR (500 MHz, $CDCl_3$) δ 8.71 (d, J=2.3 Hz, 1H), 8.45 (s, 1H), 7.80 (dd, J=8.3, 2.0 Hz, 1H), 7.62 (d, J=8.0 Hz, 1H), 7.15 (d, J=16.6 Hz, 1H), 6.93-6.91 (m, 1H), 6.60 (d, J=16.6 Hz, 1H), 6.51 (s, 1H), 6.30 (q, J=2.9 Hz, 1H).

Synthesis of Compound Represented by Structural Formula (1-2)

The cyano compound (7b) (40.0 mg, 0.19 mmol), D-cysteine hydrochloride hydrate (36.9 mg, 0.21 mmol), and potassium carbonate (39.4 mg, 0.29 mmol) were dissolved in EtOH (2 mL), distilled water (1 mL), and THF, and the mixture was stirred at 70 °C for 18 hours. The residue was then purified by automated preparative medium-pressure column chromatography (smart flash EPCLC Al-580S ULTRAPACK COLUMNS C18, $H_2O$/methanol=95/5) to obtain the compound represented by the structural formula (1-2) (14.7 mg, 0.049 mmol, 63%) as a yellow solid.

[Chem. 15]

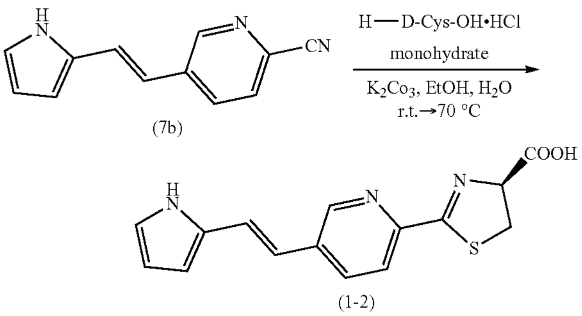

(7b) (1-2)

Identification Result of Compound Represented by Structural Formula (1-2)

1H-NMR (500 MHz, $CD_3OD$) δ 8.56 (d, J=1.7 Hz, 1H), 8.13 (d, J=8.6 Hz, 1H), 7.96 (dd, J=8.3, 2.0 Hz, 1H), 7.23 (d, J=16.6 Hz, 1H), 6.83 (m, 1H), 6.78 (d, J=16.6 Hz, 1H), 6.37 (dd, J=3.4, 1.7 Hz, 1H), 6.14 (t, J=3.2 Hz, 1H), 5.17 (t, J=9.5 Hz, 1H), 3.65-3.52 (m, 2H)

HR-MALDI-MS: m/z $[M+H]^+$ Calculated for $C_{15}H_{14}N_3O_2S$: 300.08012; Found: 300.08012.

Method for Producing Compound Represented by Structural Formula (1-3)

Synthesis of Cyano Compound (12a)

The phosphorous ylide compound (6) was synthesized using the method described in the section of "Method for Producing Compound Represented by Structural Formula (1-1)."

The phosphorous ylide compound (6) (1.68 g, 3.66 mmol) and NaH (87.9 mg, 3.66 mmol) were dissolved in THF, and the mixture was cooled to 0 °C and stirred for 1 hour. Then, N-methylpyrrole-2-carboxaldehyde (11) (100.0 mg, 0.916 mmol) was dissolved, and the mixture was stirred for 5 hours. The reaction was then quenched with distilled water. The resultant was extracted with chloroform (50 mL×3), and the organic layer was then dried over sodium sulfate and concentrated under reduced pressure. The residue was purified by silica gel column chromatography (silica gel: 50.0 g, hexane:ethyl acetate=5:1) to obtain the cyano compound (12a) (27.5 mg, 0.13 mmol, 14%) as a yellow solid.

[Chem. 16]

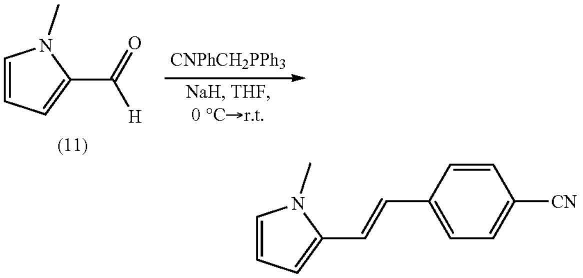

(11)

(12a)

Identification Result of Cyano Compound (12a)

1H-NMR (500 MHz, $CDCl_3$) δ=7.59 (d, J=9 Hz, 2H), 7.50 (d, J=8 Hz, 2H), 7.08 (d, J=16 Hz, 1H), 6.83 (d, J=16 Hz, 1H), 6.69 (m, 1H), 6.57 (m, 1H), 6.18 (m, 1H), 3.72 (s, 3H)

HR-MALDI-MS: m/z $[M+H]^+$ Calculated for $C_{14}H_{13}N_2$: 209.10708; Found: 209.10732.

Synthesis of Compound Represented by Structural Formula (1-3)

The cyano compound (12a) (20.0 mg, 0.10 mmol), D-cysteine hydrochloride hydrate (17.5 mg, 0.10 mmol), and sodium bicarbonate (24.2 mg, 0.23 mmol) were dissolved in MeOH (1 mL) and distilled water (1 mL). Then, 0.1 mL of 1 M NaOH was added dropwise. The mixture was stirred at 60 °C for 23 hours. The residue was then purified by automated preparative medium-pressure column chromatography (smart flash EPCLC Al-580S ULTRAPACK COLUMNS $C_{18}$, $H_2O$/methanol=95/5) to obtain the compound represented by the structural formula (1-3) (5.8 mg, 0.02 mmol, 21%) as a yellow solid.

[Chem. 17]

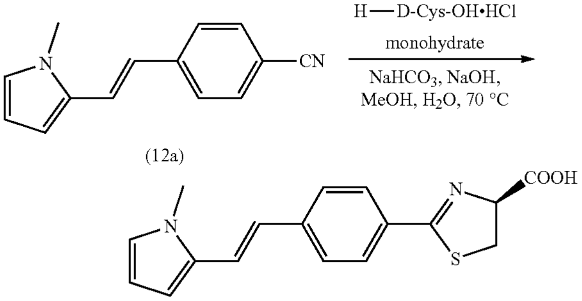

(12a)

(1-3)

Identification Result of Compound Represented by Structural Formula (1-3)

1H-NMR (500 MHz, $CD_3OD$) δ 7.80 (d, J=8.0 Hz, 2H), 7.52 (d, J=8.0 Hz, 2H), 7.20 (d, J=16.6 Hz, 1H), 6.86 (d, J=16.0 Hz, 1H), 6.68 (t, J=2.0 Hz, 1H), 6.49-6.48 (m, 1H), 6.05 (dd, J=3.7, 2.6 Hz, 1H), 5.07 (t, J=9.2 Hz, 1H), 3.70 (s, 3H), 3.68-3.56 (m, 2H)

HR-MALDI-MS: m/z $[M+H]^+$ Calculated for $C_{17}H_{17}N_2O_2S$: 313.10016; Found: 313.10052.

Method for Producing Compound Represented by Structural Formula (1-4)

Synthesis of Cyano Compound (6b)

N-methylpyrrole-2-carboxaldehyde (11) (100.0 mg, 0.916 mmol) and diethyl P-[(6-cyano-3-pyridinyl)methyl] phosphonate (349.3 mg, 1.37 mmol) were dissolved in THF (5 mL), and the mixture was cooled to 0 °C on ice. Then, NaH (76.9 mg, 3.21 mmol) was dissolved, and the mixture was refluxed by heating for 1 hour. The reaction was then quenched with distilled water. The resultant was extracted with ethyl acetate (5 mL×3), and the organic layer was then dried over sodium sulfate and concentrated under reduced pressure. The residue was purified by silica gel column chromatography (silica gel: 56.5 g, hexane:ethyl acetate=3:1) to obtain the cyano compound (12b) (147.2 mg, 0.703 mmol, 77%) as an orange solid.

[Chem. 18]

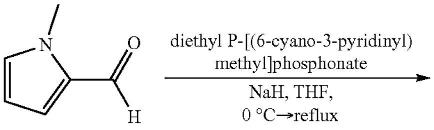

(11)

-continued

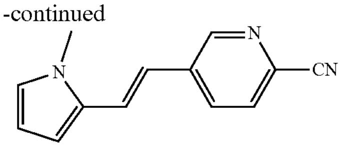

(12b)

Identification Result of Cyano Compound (12b)

1H-NMR (500 MHz, $CDCl_3$) δ=8.73 (d, J=2 Hz, 1H), 7.81 (d, J=8 Hz, 1H), 7.62 (d, J=8H, 1H), 7.15 (d, J=16 Hz, 1H), 6.79 (d, J=16 Hz, 1H), 6.73 (m, 1H), 6.63-6.62 (m, 1H), 6.20 (m, 1 Hz), 3.74 (s, 3H)

HR-MALDI-MS: m/z $[M+H]^+$ Calculated for $C_{13}H_{12}N_3$: 210.10286; Found: 210.10257.

Synthesis of Compound Represented by Structural Formula (1-4)

The cyano compound (12b) (40.0 mg, 0.19 mmol), D-cysteine hydrochloride hydrate (36.9 mg, 0.21 mmol), and potassium carbonate (39.4 mg, 0.29 mmol) were dissolved in MeOH (2 mL), distilled water (1 mL), and THF (1 mL), and the mixture was stirred at 60 °C for 24 hours. The residue was then purified by automated preparative medium-pressure column chromatography (smart flash EPCLC Al-580S ULTRAPACK COLUMNS $C_{18}$, $H_2O$/methanol=95/5) to obtain the compound represented by the structural formula (1-4) (15.9 mg, 0.051 mmol, 27%) as a yellow solid.

[Chem. 19]

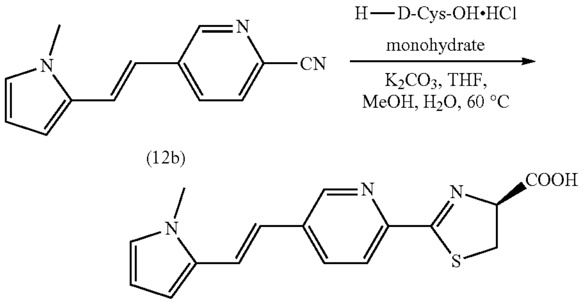

(12b)

(1-4)

Identification Result of Compound Represented by Structural Formula (1-4)

1H-NMR (500 MHz, $CD_3OD$) δ 8.60 (d, J=1.7 Hz, 1H), 8.13 (d, J=8.0 Hz, 1H), 8.03 (dd, J=8.3, 2.0 Hz, 1H), 7.34 (d, J=16.6 Hz, 1H), 6.89 (d, J=16.6 Hz, 1H), 6.73 (s, 1H), 6.58 (d, J=2.3 Hz, 1H), 6.09 (t, J=3.4 Hz, 1H), 5.17 (t, J=9.5 Hz, 1H), 3.74 (s, 3H), 3.65-3.53 (m, 2H)

HR-MALDI-MS: m/z $[M+H]^+$ Calculated for $C_{16}H_{16}N_3O_2S$: 314.09586; Found: 314.09577.

Method for Producing Compound Represented by Structural Formula (1-5)

Synthesis of Dimethylamino Compound (14)

5-Bromo-2-thiophenecarboxaldehyde (13) (1.00 g, 5.23 mmol) and dimethylamine (1.30 mL, 13.1 mmol) were dissolved in $H_2O$ (8 mL) and DMSO (2 mL), and the mixture was stirred at 80 °C for 22 hours. The reaction was then quenched with distilled water. The resultant was extracted with ethyl acetate (5 mL×3), and the organic layer was then dried over sodium sulfate and concentrated under reduced pressure. The residue was purified by silica gel column chromatography (silica gel: 25.6 g, hexane:ethyl acetate=3:1) to obtain the dimethylamino compound (14) (710.0 mg, 4.57 mmol, 87%) as a brown solid.

[Chem. 20]

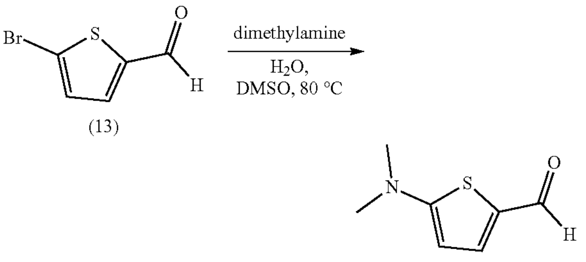

(13)

(14)

Identification Result of Dimethylamino Compound (14)

1H-NMR (500 MHz, $CDCl_3$) δ=9.50 (s, 1H), 7.48 (d, J=4.5 Hz, 1H), 5.93 (d, J=4 Hz, 1H), 3.10 (s, 6H)

HR-MALDI-MS: m/z $[M+H]^+$ Calculated for $C_{13}H_8NS$: 210.03568; Found: 210.03720.

Synthesis of Cyano Compound (15)

The dimethylamino compound (14) (50.0 mg, 0.32 mmol) and diethyl P-[(6-cyano-3-pyridinyl)methyl]phosphonate (122.8 mg, 0.48 mmol) were dissolved in THF (5 mL), and the mixture was cooled to 0 °C on ice. Then, NaH (27.0 mg, 1.13 mmol) was dissolved, and the mixture was refluxed by heating for 1 hour. The reaction was then quenched with distilled water. The resultant was extracted with ethyl acetate (5 mL×3), and the organic layer was then dried over sodium sulfate and concentrated under reduced pressure. The residue was purified by silica gel column chromatography (silica gel: 46.5 g, hexane:ethyl acetate=2:1) to obtain the cyano compound (15) (69.6 mg, 0.087 mmol, 27%) as a red solid.

[Chem. 21]

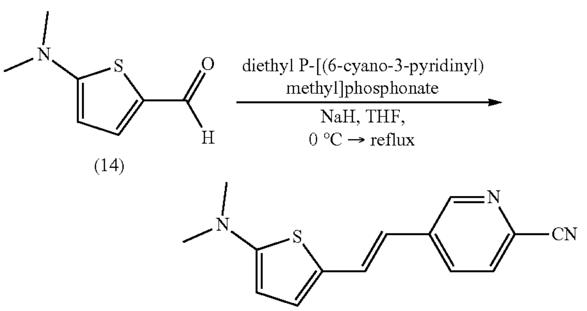

(14)

(15)

Identification Result of Cyano Compound (15)

1H-NMR (500 MHz, $CDCl_3$) δ 8.64 (d, J=2.3 Hz, 1H), 7.72 (dd, J=8.0, 2.3 Hz, 1H), 7.56 (d, J=8.6 Hz, 1H), 7.27 (d, J=16.0 Hz, 1H), 6.90 (d, J=4.0 Hz, 1H), 6.38 (d, J=16.0 Hz, 1H), 5.78 (d, J=4.0 Hz, 1H), 3.02 (s, 6H)

HR-MALDI-MS: m/z $[M+H]^+$ Calculated for $C_{14}H_{14}N_3S$: 256.09033; Found: 256.09029.

Synthesis of Compound Represented by Structural Formula (1-5)

The cyano compound (15) (45.0 mg, 0.18 mmol), D-cysteine hydrochloride hydrate (34.0 mg, 0.19 mmol), and potassium carbonate (36.5 mg, 0.27 mmol) were dissolved in MeOH (2 mL), distilled water (1 mL), and THF (1 mL), and the mixture was stirred at 60 °C for 18 hours. The residue was then purified by automated preparative medium-pressure column chromatography (smart flash EPCLC Al-580S ULTRAPACK COLUMNS $C_{18}$, $H_2O$/methanol=95/5) to obtain the compound represented by the structural formula (1-5) (33.7 mg, 0.094 mmol, 53%) as a red solid.

[Chem. 22]

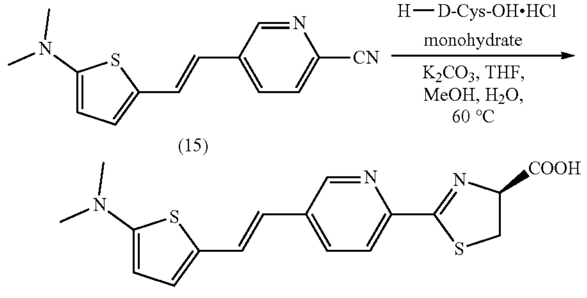

(15)

(1-5)

Identification Result of Compound Represented by Structural Formula (1-5)

1H-NMR (500 MHz, $CD_3OD$) δ 8.52 (d, J=1.7 Hz, 1H), 8.10 (d, J=8.0 Hz, 1H), 7.91 (dd, J=8.3, 2.0 Hz, 1H), 7.38 (d, J=15.5 Hz, 1H), 6.89 (d, J=4.0 Hz, 1H), 6.48 (d, J=16.0 Hz, 1H), 5.83 (d, J=4.0 Hz, 1H), 5.16 (t, J=9.5 Hz, 1H), 3.64-3.53 (m, J=2H), 2.98 (s, 6H)

HR-MALDI-MS: m/z $[M+H]^+$ Calculated for $C_{17}H_{18}N_3O_2S_2$: 360.08296; Found: 360.08349.

Method for Producing Compound Represented by Structural Formula (1-6)

Synthesis of Dimethylamino Compound (17)

5-Bromo-2-furaldehyde (16) (700 mg, 4.00 mmol) and dimethylamine (1.26 mL, 12.0 mmol) were dissolved in $H_2O$ (8 mL) and DMSO (2 mL), and the mixture was stirred at 80 °C for 22 hours. The reaction was then quenched with distilled water. The resultant was extracted with ethyl acetate (25 mL×3), and the organic layer was then dried over sodium sulfate and concentrated under reduced pressure. The residue was purified by silica gel column chromatography (silica gel: 41.4 g, hexane:ethyl acetate=1:1) to obtain the dimethylamino compound (17) (387 mg, 2.21 mmol, 55%) as a blue oily substance.

[Chem. 23]

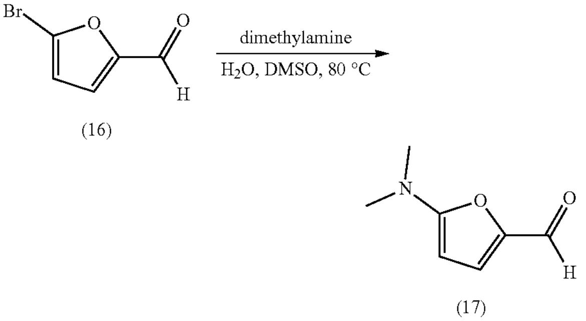

(16)

(17)

Identification Result of Dimethylamino Compound (17)

1H-NMR (500 MHz, $CDCl_3$) δ 8.97 (s, 1H), 7.20 (s, 1H), 5.23 (d, J=4.0 Hz, 1H), 3.08 (s, 6H)

Synthesis of Cyano Compound (18)

The dimethylamino compound (17) (50.0 mg, 0.36 mmol) and diethyl P-[(6-cyano-3-pyridinyl)methyl]phosphonate (137.0 mg, 0.54 mmol) were dissolved in THF (5 mL), and the mixture was cooled to 0 °C on ice. Then, NaH (30.2 mg, 1.26 mmol) was dissolved, and the mixture was refluxed by heating at 80 °C for 1 hour. The reaction was then quenched with distilled water. The resultant was extracted with ethyl acetate (25 mL×3), and the organic layer was then dried over sodium sulfate and concentrated under reduced pressure. The residue was purified by silica gel column chromatography (silica gel: 21.5 g, hexane:ethyl acetate=4:1) to obtain the cyano compound (18) (37.5 mg, 0.16 mmol, 44%) as a red solid.

[Chem. 24]

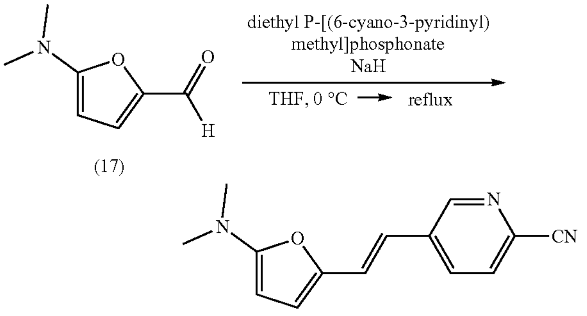

(17)

(18)

Identification Result of Cyano Compound (18)

1H-NMR (500 MHz, $CDCl_3$) δ 8.65 (d, J=2.3 Hz, 1H), 7.71 (dd, J=8.0, 2.3 Hz, 1H), 7.55 (d, J=8.6 Hz, 1H), 6.87 (d, J=16.0 Hz, 1H), 6.53 (d, J=15.5 Hz, 1H), 6.46 (d, J=3.4 Hz, 1H), 5.10 (d, J=3.4 Hz, 1H), 2.97 (s, 6H)

Synthesis of Compound Represented by Structural Formula (1-6)

The cyano compound (18) (25.0 mg, 0.10 mmol), D-cysteine hydrochloride hydrate (27.5 mg, 0.16 mmol), and potassium carbonate (22.1 mg, 0.16 mmol) were dissolved in MeOH (2 mL), distilled water (1 mL), and THF (1 mL), and the mixture was stirred at 60 °C for 18 hours. The residue was then purified by automated preparative medium-pressure column chromatography (smart flash EPCLC AI-580S ULTRAPACK COLUMNS $C_{18}$, $H_2O$/methanol=95/5) to obtain the compound represented by the structural formula (1-6) (10.5 mg, 0.031 mmol, 31%) as a red solid.

[Chem. 25]

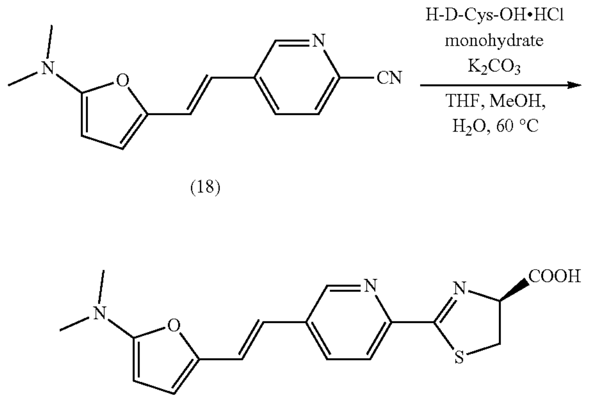

(18)

(1-6)

Identification Result of Compound Represented by Structural Formula (1-6)

1H-NMR (500 MHz, $CD_3OD$) δ 8.53 (d, J=9.2 Hz, 1H), 8.08-8.07 (m, 1H), 7.91 (d, J=8.0 Hz, 1H), 7.02 (d, J=16.0 Hz, 1H), 6.62 (d, J=16.0 Hz, 1H), 6.45 (d, J=2.3 Hz, 1H), 5.18 (t, J=9.2 Hz, 1H), 3.64-3.52 (m, 2H), 2.93 (s, 6H)

Method for Producing Compound Represented by Structural Formula (1-7)

Synthesis of N,N-Dimethylthiazole-2-amine (20)

Thiazole-2-amine (19) (1.00 g, 10.0 mmol) was dissolved in THF (30 mL), iodomethane (1.80 mL, 29.7 mmol) was added and stirred. The mixture solution was cooled to 0 °C, NaH (1.50 g, 39.6 mmol) was added in small portions, and the mixture was stirred for 70 minutes. Methanol was added on an ice bath to quench the reaction. The resultant was extracted with chloroform (100 mL×3). The organic layer was washed with saturated brine solution and then concentrated under reduced pressure. The resulting residue was then purified by silica gel column chromatography (silica gel: 51.2 g, hexane:ethyl acetate=2:1) to obtain N,N-dimethylthiazole-2-amine (20) (842 mg, 6.57 mmol, 66%) as a brown oily substance.

[Chem. 26]

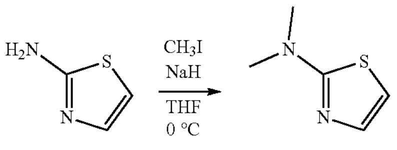

(19) (20)

Identification Result of N,N-Dimethylthiazole-2-amine (20)

1H-NMR (500 MHz, $CDCl_3$) δ 7.19 (d, J=3.4 Hz, 1H), 6.50 (d, J=3.4 Hz, 1H), 3.11 (s, 6H)

Synthesis of 2-(Dimethylamino)thiazole-5-carbaldehyde (21)

N,N-Dimethylthiazole-2-amine (20) (461 mg, 3.60 mmol) was dissolved in anhydrous THF (30 mL), and the mixture was cooled to −80 °C and stirred under an argon atmosphere. LDA (2.0 M, 3.60 mL, 7.19 mmol) was added in small portions to this mixture solution, and the mixture was stirred for 60 minutes. Then, anhydrous DMF (1.25 mL) was added, and the mixture was allowed to warm to room temperature and stirred for an additional 90 minutes. After confirming the consumption of the starting material, water was added on an ice bath to quench the reaction. The resultant was extracted with chloroform (50 mL×3), washed with saturated brine solution, and then concentrated under reduced pressure. The resulting residue was then purified by silica gel column chromatography (silica gel: 21.5 g, hexane:ethyl acetate=4:1) to obtain 2-(dimethylamino)thiazole-5-carbaldehyde (21) (256.9 mg, 1.64 mmol, 46%) as a yellow solid.

[Chem. 27]

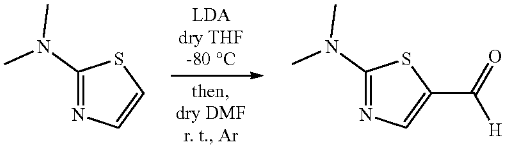

(20) (21)

Identification Result of 2-(Dimethylamino)thiazole-5-carbaldehyde (21)

1H-NMR (500 MHz, $CDCl_3$) δ 9.68 (s, 1H), 7.87 (s, 1H), 3.23 (s, 6H)

Synthesis of Cyano Compound (22a)

2-(Dimethylamino)thiazole-5-carbaldehyde (21) (50.0 mg, 0.36 mmol) and diethyl P-[(6-cyano-3-pyridinyl)methyl]phosphonate (137.0 mg, 0.54 mmol) were dissolved in THF (5 mL), and the mixture was cooled to 0 °C on ice. Then, NaH (30.2 mg, 1.26 mmol) was dissolved, and the mixture was refluxed by heating at 80 °C for 1 hour. The reaction was then quenched with distilled water. The resultant was extracted with ethyl acetate (25 mL×3), and the organic layer was then dried over sodium sulfate and concentrated under reduced pressure. The residue was purified by silica gel column chromatography (silica gel: 21.5 g, hexane:ethyl acetate=4:1) to obtain the cyano compound (22a) (37.5 mg, 0.16 mmol, 44%) as a red solid.

[Chem. 28]

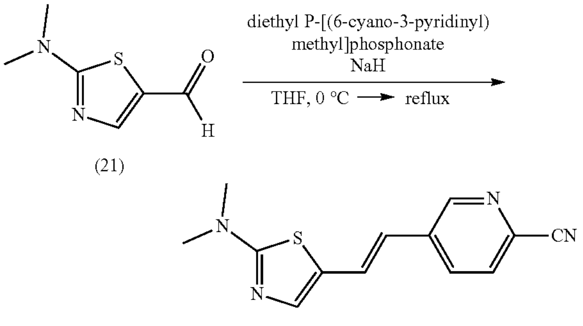

(21)

(22a)

Identification Result of Cyano Compound (22a)

1H-NMR (500 MHz, $CDCl_3$) δ 8.66 (d, J=2.3 Hz, 1H), 7.76 (dd, J=8.3, 2.0 Hz, 1H), 7.60 (d, J=8.6 Hz, 1H), 7.30 (d, J=5.2 Hz, 1H), 7.27 (s, 1H), 6.38 (d, J=16.0 Hz, 1H), 3.18 (s, 6H)

Synthesis of Compound Represented by Structural Formula (1-7)

The cyano compound (22a) (22.1 mg, 0.086 mmol), D-cysteine hydrochloride hydrate (22.7 mg, 0.13 mmol), and potassium carbonate (18.0 mg, 0.13 mmol) were dissolved in MeOH (2 mL), distilled water (1 mL), and THF (1 mL), and the mixture was stirred at 60 °C for 20 hours. The residue was then purified by automated preparative medium-pressure column chromatography (smart flash EPCLC Al-580S ULTRAPACK COLUMNS $C_{18}$, $H_2O$/methanol=95/5) to obtain the compound represented by the structural formula (1-7) (20.7 mg, 0.058 mmol, 67%) as a yellow solid.

[Chem. 29]

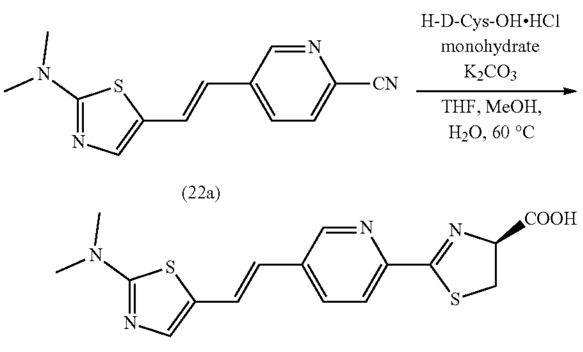

(22a)

(1-7)

Identification Result of Compound Represented by Structural Formula (1-7)

1H-NMR (500 MHz, $CD_3OD$) δ 8.58 (d, J=1.7 Hz, 1H), 8.12 (d, J=8.6 Hz, 1H), 7.97 (dd, J=8.3, 2.0 Hz, 1H), 7.45 (d, J=16.0 Hz, 1H), 7.27 (s, 1H), 6.55 (d, J=16.0 Hz, 1H), 5.23 (t, J=9.5 Hz, 1H), 3.63 (t, J=10.3 Hz, 1H), 3.56 (t, J=10.5 Hz, 1H), 3.15 (s, 6H)

Method for Producing Compound Represented by Structural Formula (1-8)

Synthesis of Cyano Compound (22b)

2-(Dimethylamino)thiazole-5-carbaldehyde (21) (50.0 mg, 0.32 mmol) and diethyl P-[(6-cyanophenyl)methyl] phosphonate (131.6 mg, 0.48 mmol) were dissolved in THF (5 mL), and the mixture was cooled to 0 °C on ice. Then, NaH (26.9 mg, 1.12 mmol) was dissolved, and the mixture was refluxed by heating at 80 °C for 3 hours. The reaction was then quenched with distilled water. The resultant was extracted with ethyl acetate (30 mL×3), and the organic layer was then dried over sodium sulfate and concentrated under reduced pressure. The residue was purified by silica gel column chromatography (silica gel: 17.5 g, hexane:ethyl acetate=4:1) to obtain the cyano compound (22b) (69.7 mg, 0.27 mmol, 85%) as a yellow solid.

[Chem. 30]

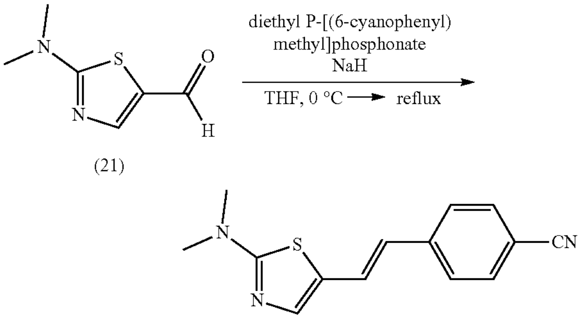

(21)

(22b)

Identification Result of Cyano Compound (22b)

1H-NMR (500 MHz, $CDCl_3$) δ 7.57 (d, J=8.6 Hz, 2H), 7.44 (d, J=8.6 Hz, 2H), 7.25 (s, 1H), 7.20 (d, J=15.5 Hz, 1H), 6.42 (d, J=16.0 Hz, 1H), 3.16 (s, 6H)

Synthesis of Compound Represented by Structural Formula (1-8)

The cyano compound (22b) (25.0 mg, 0.098 mmol), D-cysteine hydrochloride hydrate (25.8 mg, 0.15 mmol), and sodium bicarbonate (24.7 mg, 0.29 mmol) were dissolved in MeOH (2 mL), distilled water (1 mL), and THF (1 mL). Then, 2 drops of 1M NaOH were added dropwise. The mixture was stirred at 60 °C for 15 hours. The residue was then purified by automated preparative medium-pressure column chromatography (smart flash EPCLC Al-580S ULTRAPACK COLUMNS $C_{18}$, $H_2O$/methanol=95/5) to obtain the compound represented by the structural formula (1-8) (20.5 mg, 0.057 mmol, 58%) as a yellow solid.

[Chem. 31]

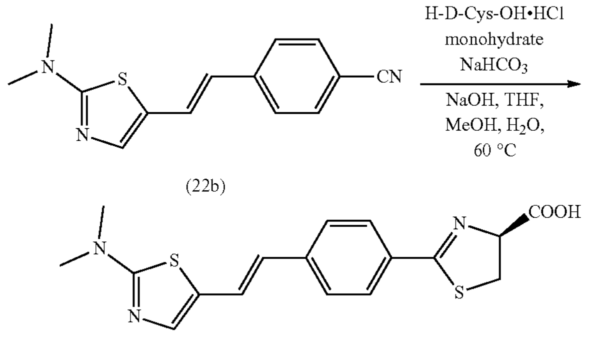

(22b)

(1-8)

Identification Result of Compound Represented by Structural Formula (1-8)

1H-NMR (500 MHz, $CD_3OD$) δ 7.81 (d, J=8.6 Hz, 2H), 7.48 (d, J=8.0 Hz, 2H), 7.31 (d, J=15.5 Hz, 1H), 7.21 (s, 1H), 6.54 (d, J=16.0 Hz, 1H), 5.08 (t, J=9.5 Hz, 1H), 3.69-3.58 (m, 2H), 3.14 (s, 7H)

Method for Producing Compound Represented by Structural Formula (1-9)

Synthesis of N,N-Dimethylthiazole-5-amine (24)

5-Bromothiazole (23) (750 mg, 4.57 mmol) was dissolved in 1,2-dimethoxyethane (DME) (25 mL) and DMF (15 mL). NHMe2 (50% in water, 1.52 mL, 13.7 mmol) was added and stirred. To the mixture, tBuONa (887.5 mg, 9.14 mmol), $Rh(Cod)_2BF_4$ (18.6 mg, 457 umol), and 1,3-diisopropylimidazolium chloride (34.5 mg, 0.18 mmol) were added. The mixture was stirred at 80 °C under an argon atmosphere for 16 hours. After confirming the disappearance of the starting material, the mixture was cooled to room temperature and filtered with silica under suction. The filtrate was washed with water and brine solution. The organic layer was concentrated, and the residue was purified by silica gel column chromatography (silica gel: 25.6 g, hexane:ethyl acetate=3:1) to obtain N,N-dimethylthiazole-5-amine (24) (365 mg, 2.85 mmol, 62%) as a brown oily substance.

[Chem. 32]

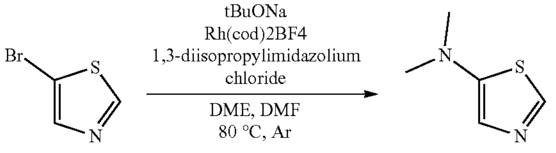

(23) (24)

Identification Result of N,N-Dimethylthiazole-5-amine (24)

1H-NMR (500 MHz, $CDCl_3$) δ 8.08 (s, 1H), 6.85 (s, 1H), 2.92 (s, 6H)

Synthesis of 5-(Dimethylamino)thiazole-2-carbaldehyde (25)

N,N-Dimethylthiazole-5-amine (24) (450 mg, 3.51 mmol) was dissolved in anhydrous THF (20 mL), and the mixture was cooled to −80 °C and stirred under an argon atmosphere. LiHMDS (1.3 M, 3.51 mL, 4.56 mmol) was added in small portions to this mixture solution, and the mixture was stirred for 60 minutes. Then, anhydrous DMF (1.5 mL) was added, and the mixture was allowed to warm to room temperature and stirred for an additional 90 minutes. After confirming the consumption of the starting material, water was added on an ice bath to quench the reaction. The resultant was extracted with ethyl acetate (50 mL×3) and washed with saturated brine solution. The resultant was then concentrated under reduced pressure to obtain 5-(dimethylamino)thiazole-2-carbaldehyde (25) (446.5 mg, 2.86 mmol, 81%) as a brown solid.

[Chem. 33]

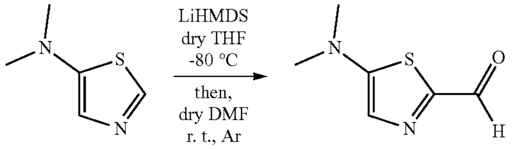

(24) (25)

Identification Result of 5-(Dimethylamino)thiazole-2-carbaldehyde (25)

1H-NMR (500 MHz, $CDCl_3$) δ 9.68 (s, 1H), 7.06 (s, 1H), 3.13 (s, 6H)

Synthesis of Cyano Compound (26a)

5-(Dimethylamino)thiazole-2-carbaldehyde (25) (75.0 mg, 0.48 mmol) and diethyl P-[(6-cyano-3-pyridinyl) methyl]phosphonate (183 mg, 0.72 mmol) were dissolved in THF (5 mL), and the mixture was cooled to 0 °C on ice. Then, NaH (40.3 mg, 1.68 mmol) was dissolved, and the mixture was refluxed by heating at 80 °C for 20 minutes. The reaction was then quenched with distilled water. The resultant was extracted with ethyl acetate (30 mL×3), and the organic layer was then dried over sodium sulfate and concentrated under reduced pressure. The residue was purified by silica gel column chromatography (silica gel: 24.5 g, hexane:ethyl acetate=2:1) to obtain the cyano compound (26a) (44.6 mg, 0.17 mmol, 36%) as an orange solid.

[Chem. 34]

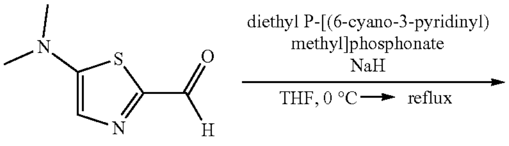

(25)

-continued

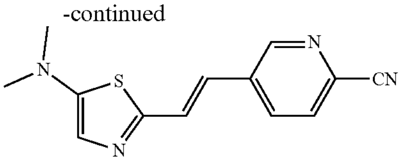

(26a)

Identification Result of Cyano Compound (26a)

1H-NMR (500 MHz, $CDCl_3$) δ 8.73 (d, J=2.3 Hz, 1H), 7.84 (dd, J=8.0, 2.3 Hz, 1H), 7.64 (d, J=8.6 Hz, 1H), 7.31 (d, J=16.0 Hz, 1H), 6.90 (d, J=16.0 Hz, 1H), 6.80 (s, 1H), 3.03 (s, 6H)

Synthesis of Compound Represented by Structural Formula (1-9)

The cyano compound (26a) (25 mg, 0.098 mmol), D-cysteine hydrochloride hydrate (25.7 mg, 0.15 mmol), and potassium carbonate (20.7 mg, 0.15 mmol) were dissolved in MeOH (2 mL), distilled water (1 mL), and THF (1 mL), and the mixture was stirred at 60 °C for 20 hours. The residue was then purified by automated preparative medium-pressure column chromatography (smart flash EPCLC Al-580S ULTRAPACK COLUMNS $C_{18}$, $H_2O$/methanol=95/5) to obtain the compound represented by the structural formula (1-9) (19.2 mg, 0.053 mmol, 54%) as an orange solid.

[Chem. 35]

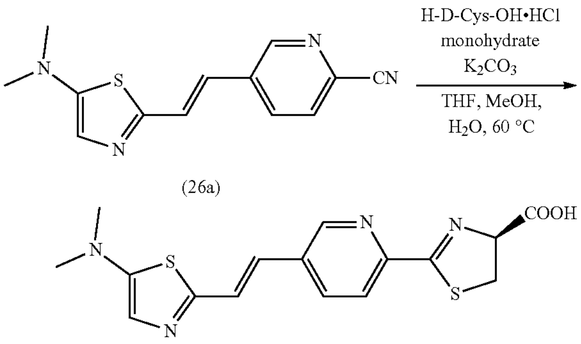

(26a)

(1-9)

Identification Result of Compound Represented by Structural Formula (1-9)

1H-NMR (500 MHz, $CD_3OD$) δ 8.65-8.64 (m, 1H), 8.17 (d, J=8.0 Hz, 1H), 8.05 (dd, J=8.6, 2.3 Hz, 1H), 7.35 (d, J=16.0 Hz, 1H), 7.08 (d, J=16.6 Hz, 1H), 6.79 (s, 1H), 5.18 (t, J=9.7 Hz, 1H), 3.63 (t, J=10.3 Hz, 1H), 3.55 (t, J=10.0 Hz, 1H), 3.01 (s, 6H)

Method for Producing Compound Represented by Structural Formula (1-10)

Synthesis of Cyano Compound (26b)

5-(Dimethylamino)thiazole-2-carbaldehyde (25) (50.0 mg, 0.32 mmol) and diethyl P-[(5-cyano-2-pyridinyl) methyl]phosphonate (122 mg, 0.48 mmol) were dissolved in THF (5 mL), and the mixture was cooled to 0 °C on ice. Then, NaH (26.9 mg, 1.12 mmol) was dissolved, and the mixture was refluxed by heating at 80 °C for 30 minutes. The reaction was then quenched with distilled water. The resultant was extracted with ethyl acetate (30 mL×3), and the organic layer was then dried over sodium sulfate and concentrated under reduced pressure. The residue was purified by silica gel column chromatography (silica gel: 19.5 g, hexane:ethyl acetate=1:1) to obtain the cyano compound (26b) (33.3 mg, 0.13 mmol, 41%) as an orange solid.

[Chem. 36]

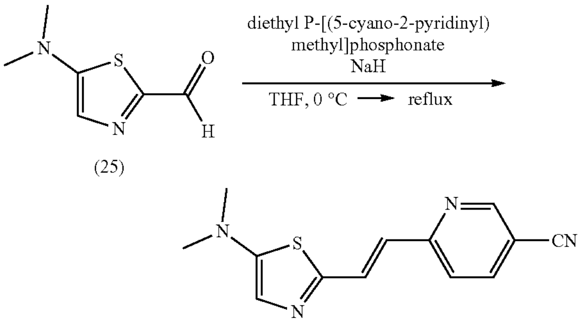

(25)

(26b)

Identification Result of Cyano Compound (26b)

1H-NMR (500 MHz, $CDCl_3$) δ 8.82 (d, J=1.7 Hz, 1H), 8.06 (dd, J=8.3, 2.0 Hz, 1H), 7.78 (d, J=16.0 Hz, 1H), 7.59 (d, J=8.0 Hz, 1H), 7.07 (d, J=15.5 Hz, 1H), 6.86 (s, 1H), 3.04 (s, 6H)

Synthesis of Compound Represented by Structural Formula (1-10)

The cyano compound (26b) (20.0 mg, 0.078 mmol), D-cysteine hydrochloride hydrate (20.6 mg, 0.12 mmol), and sodium bicarbonate (19.7 mg, 0.23 mmol) were dissolved in MeOH (2 mL), distilled water (1 mL), and THF (1 mL). Then, 2 drops of 1M NaOH were added. The mixture was stirred at 60 °C for 20 hours. The residue was then purified by automated preparative medium-pressure column chromatography (smart flash EPCLC Al-580S ULTRAPACK COLUMNS $C_{18}$, $H_2O$/methanol=95/5) to obtain the compound represented by the structural formula (1-10) (15.3 mg, 0.042 mmol, 54%) as an orange solid.

[Chem. 37]

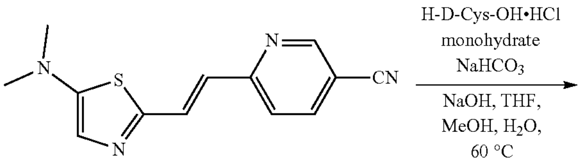

(26b)

-continued

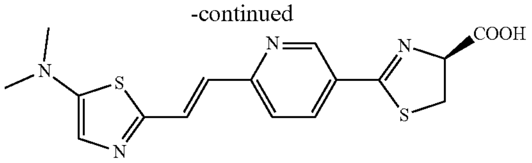

(1-10)

Identification Result of Compound Represented by Structural Formula (1-10)

1H-NMR (500 MHz, $CD_3OD$) δ 8.95 (d, J=2.3 Hz, 1H), 8.21 (dd, J=8.6, 1.7 Hz, 1H), 7.67 (d, J=15.5 Hz, 1H), 7.58 (d, J=8.6 Hz, 1H), 7.09 (d, J=16.0 Hz, 1H), 6.82 (s, 1H), 5.14 (t, J=8.9 Hz, 1H), 3.46-3.43 (m, 2H), 3.03 (s, 6H)

Measurement of Emission Spectrum

The emission spectra were measured using the luminescent substrates represented by the structural formulas (1-1) to (1-10) synthesized as described above and the luminescent substrate represented by the structural formula (a) below. The luminescent substrate represented by the structural formula (a) was prepared according to "Synthesis of Luminescent Substrate C" in WO 2021/193069 A1 (PTL 4).

[Chem. 38]

(a)

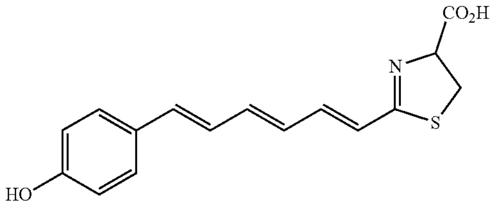

Figure 2:
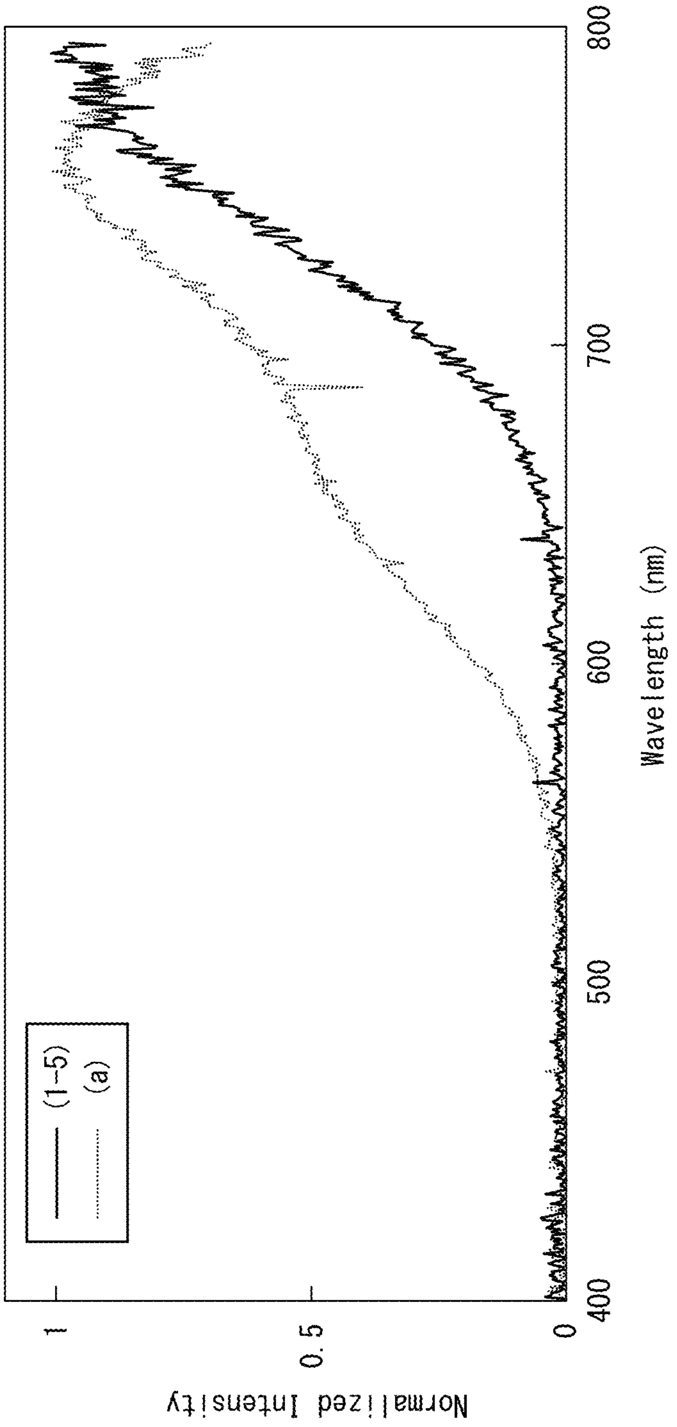
FIG. 2 illustrates emission spectra normalized so that the maximum emission intensity was 1 in a luminescent system using the compound represented by the structural formula (1-5), or the compound represented by the structural formula (a) as the luminescent substrate.
Figure 3:
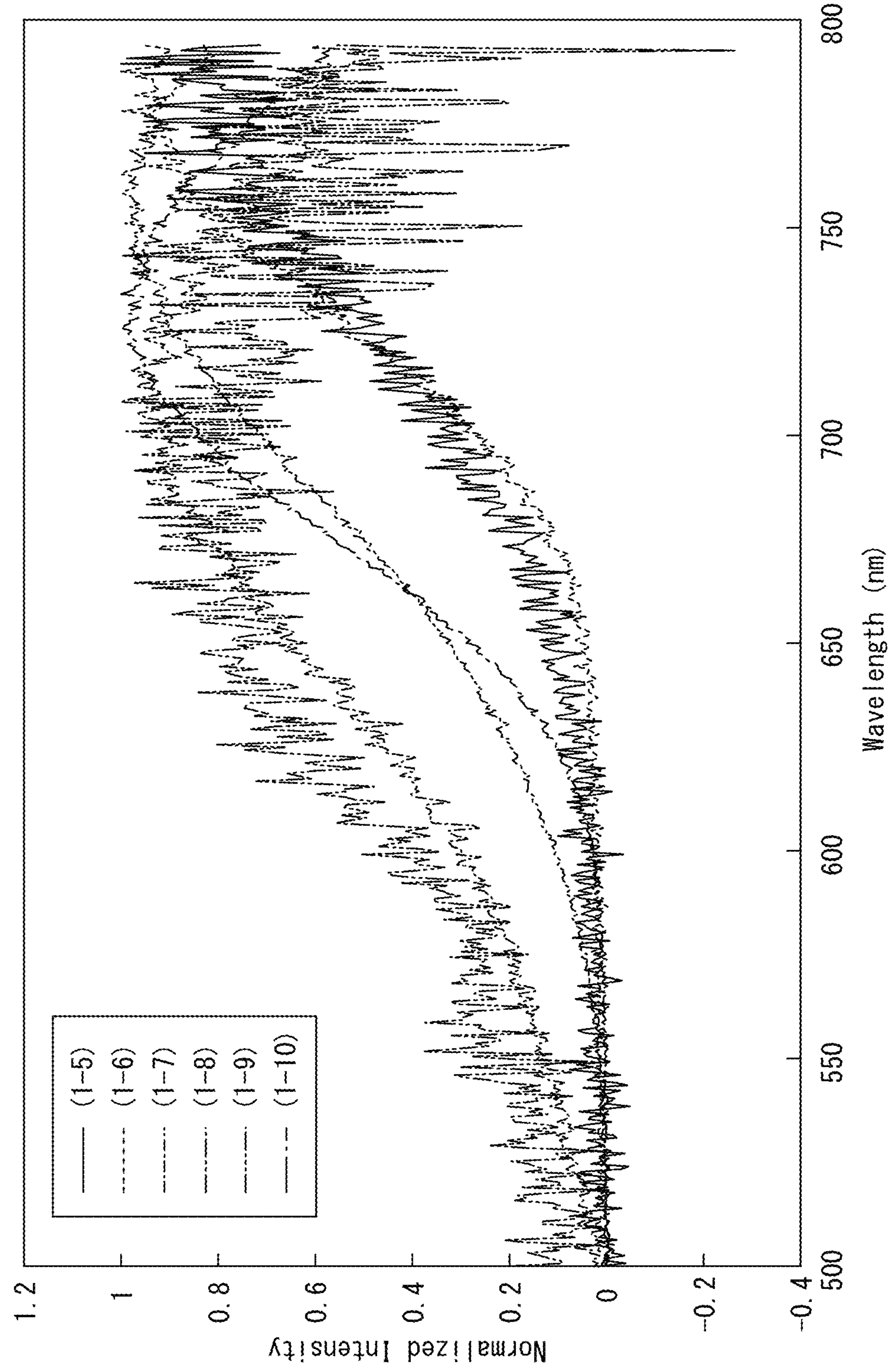
FIG. 3 illustrates emission spectra normalized so that the maximum emission intensity was 1 in a luminescent system using the compound represented by the structural formula (1-5), the compound represented by the structural formula (1-6), the compound represented by the structural formula (1-7), the compound represented by the structural formula (1-8), the compound represented by the structural formula (1-9), or the compound represented by the structural formula (1-10) as the luminescent substrate.

Specifically, 5 μL of 500 mM potassium phosphate buffer (KPB, pH 8.0), 5 μL of a 100 μM solution of each luminescent substrate, 5 μL of a 1 mg/mL solution of natural firefly luciferase (Fluc), and 10 μL of a 10 mM ATP magnesium salt solution were mixed, and the emission spectrum was measured for 180 seconds using a luminescence measurement device (AB-1850 manufactured by ATTO Corporation). However, the substrate concentration for the luminescent substrate represented by the structural formula (a) was set to 1 mM, and the substrate concentration for the luminescent substrate represented by the structural formula (1-6) was set to 10 mM. The results are shown in FIGS. 1 to 3. Note that FIGS. 1 to 3 illustrate emission spectra normalized so that the maximum emission intensity was 1. The wavelengths of maximum emission intensity ($\lambda_{max}$) are summarized in Table 1.

TABLE 1

| Luminescent substrate | Maximum emission wavelength for each substrate (nm) |
|---|---|
| Compound of structural formula (1-1) | 640 |
| Compound of structural formula (1-2) | 660 |
| Compound of structural formula (1-3) | 640 |
| Compound of structural formula (1-4) | 660 |
| Compound of structural formula (1-5) | 790 |

TABLE 1-continued

| Luminescent substrate | Maximum emission wavelength for each substrate (nm) |
|---|---|
| Compound of structural formula (1-6) | 790 |
| Compound of structural formula (1-7) | 710 |
| Compound of structural formula (1-8) | 680 |
| Compound of structural formula (1-9) | 760 |
| Compound of structural formula (1-10) | 730 |
| Compound of structural formula (a) | 765 |

Results

As shown in FIG. 1 and Table 1, the luminescent substrates represented by the structural formulas (1-1) to (1-4) are capable of emitting long-wavelength light of about 640 to 660 nm, and are effective for the visualization of deep areas inside living organisms.

In addition, as shown in FIG. 2, FIG. 3, and Table 1, the luminescent substrates represented by the structural formulas (1-5) or (1-6) are capable of emitting long-wavelength light of about 790 nm, and are particularly effective for the visualization of deep areas inside living organisms. Even the luminescent substrate represented by the structural formula (a), which had the longest emission wavelength to date, had an emission wavelength of about 765 nm. Therefore, the luminescent substrates represented by the structural formulas (1-5) or (1-6) have the longest emission wavelengths.

Moreover, as shown in FIG. 3 and Table 1, the luminescent substrates represented by the structural formulas (1-7) to (1-10) are capable of emitting long-wavelength light of about 680 to 760 nm, and are effective for the visualization of deep areas inside living organisms.

INDUSTRIAL APPLICABILITY

The heterocyclic compound and salt thereof of the present disclosure can be used as luminescent substrates in firefly bioluminescent systems.

The invention claimed is:

1. A heterocyclic compound represented by the following general formula (1):

(1)

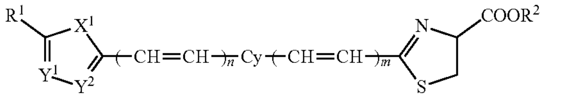

where Cy is represented by the following general formula (2-1) or (2-2):

(2-1)

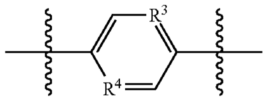

(2-2)

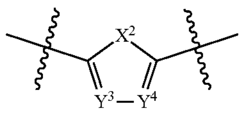

$R^1$ is —$NR^5R^6$, —$OR^7$, or hydrogen, and $R^5$, $R^6$, and $R^7$ are each independently hydrogen or an alkyl group having 1 to 4 carbon atoms; $R^5$ and $R^6$ may bond together to form a ring, or one of $R^5$ and $R^6$ may bond with $Y^1$ to form a ring, $R^2$ is hydrogen or an alkyl group having 1 to 4 carbon atoms, $R^3$ and $R^4$ are each independently CH or N, $X^1$ and $X^2$ are each independently S, O, $NR^8$, or $CH_2$, $Y^1$, $Y^2$, $Y^3$, and $Y^4$ are each independently N or $CR^8$, where $R^8$ is each independently hydrogen, an alkyl group having 1 to 4 carbon atoms, an alkenyl group having 2 to 4 carbon atoms, or an acyl group having 2 to 4 carbon atoms, and n and m are each independently an integer of 0 to 3, or a salt thereof.

2. The heterocyclic compound according to claim 1, wherein $X^1$ is S, O, or $NR^8$.

3. The heterocyclic compound according to claim 1, wherein $Y^1$ and $Y^2$ are each independently $CR^8$.

4. The heterocyclic compound according to claim 1, wherein Cy is represented by the above general formula (2-1).

5. The heterocyclic compound according to claim 1, which is represented by any of the following structural formulas (1-1) to (1-10):

(1-1)

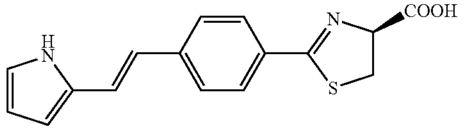

(1-2)

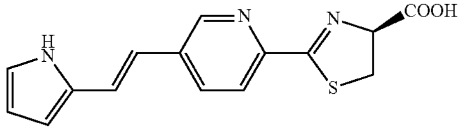

(1-3)

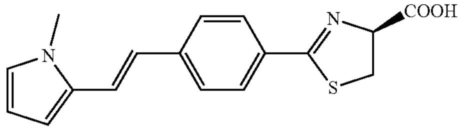

(1-4)

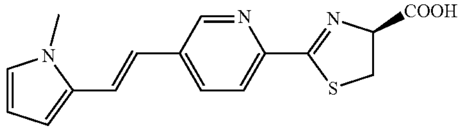

-continued (1-5)

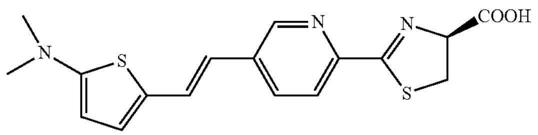

(1-6)

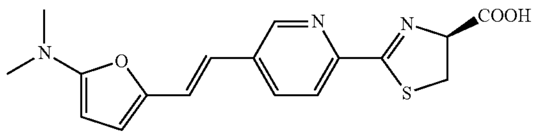

(1-7)

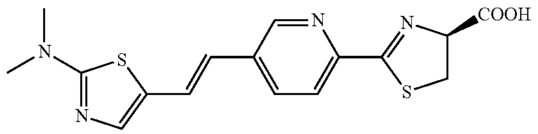

(1-8)

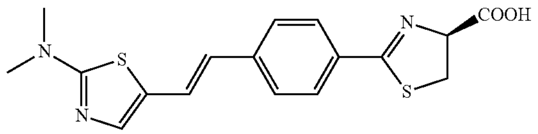

(1-9)

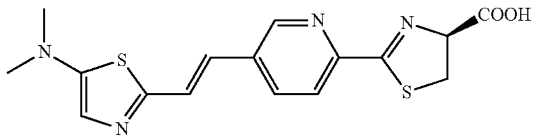

(1-10)

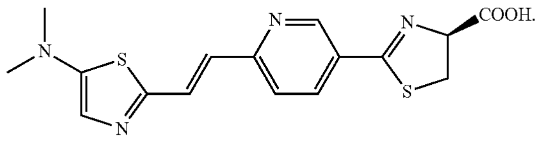

6. A salt of the heterocyclic compound according to claim 1.

7. A luminescent substrate composition comprising the heterocyclic compound according to claim 1.

8. A luminescent substrate composition comprising the salt according to claim 6.

9. The heterocyclic compound according to claim 1, wherein at least one of n and m is not 0.

* * * * *